United States Patent
Alterovitz

(10) Patent No.: US 11,529,354 B2
(45) Date of Patent: Dec. 20, 2022

(54) METHODS AND COMPOSITIONS FOR THE TREATMENT OF TUBERCULOSIS

(71) Applicant: PRESIDENT AND FELLOWS OF HARVARD COLLEGE, Cambridge, MA (US)

(72) Inventor: Gil Alterovitz, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 86 days.

(21) Appl. No.: 16/643,956

(22) PCT Filed: Sep. 5, 2018

(86) PCT No.: PCT/US2018/049463
§ 371 (c)(1),
(2) Date: Mar. 3, 2020

(87) PCT Pub. No.: WO2019/050890
PCT Pub. Date: Mar. 14, 2019

(65) Prior Publication Data
US 2021/0137932 A1    May 13, 2021

Related U.S. Application Data

(60) Provisional application No. 62/554,040, filed on Sep. 5, 2017.

(51) Int. Cl.
| | | |
|---|---|---|
| *A61K 31/536* | (2006.01) | |
| *A61P 31/06* | (2006.01) | |
| *A61K 31/085* | (2006.01) | |
| *A61K 31/138* | (2006.01) | |
| *A61K 31/353* | (2006.01) | |
| *A61K 31/4045* | (2006.01) | |
| *A61K 31/4184* | (2006.01) | |
| *A61K 31/429* | (2006.01) | |
| *A61K 31/4422* | (2006.01) | |
| *A61K 31/4439* | (2006.01) | |
| *A61K 31/538* | (2006.01) | |
| *A61K 31/554* | (2006.01) | |

(52) U.S. Cl.
CPC .......... *A61K 31/536* (2013.01); *A61K 31/085* (2013.01); *A61K 31/138* (2013.01); *A61K 31/353* (2013.01); *A61K 31/4045* (2013.01); *A61K 31/4184* (2013.01); *A61K 31/429* (2013.01); *A61K 31/4422* (2013.01); *A61K 31/4439* (2013.01); *A61K 31/538* (2013.01); *A61K 31/554* (2013.01); *A61P 31/06* (2018.01)

(58) Field of Classification Search
CPC .. A61K 31/536; A61K 31/085; A61K 31/138; A61K 31/353; A61K 31/4045; A61K 31/4184; A61K 31/429; A61K 31/4422; A61K 31/4439; A61K 31/538; A61K 31/554; A61P 31/06
See application file for complete search history.

(56) References Cited

U.S. PATENT DOCUMENTS

| | | |
|---|---|---|
| 6,384,041 B1 | 5/2002 | Hutchison et al. |
| 8,669,283 B2 | 3/2014 | Sieber et al. |
| 2007/0276009 A1 | 11/2007 | Ni et al. |
| 2009/0163545 A1 | 6/2009 | Goldfarb |
| 2011/0077250 A1 | 3/2011 | Ryder |
| 2013/0196991 A1 | 8/2013 | Ivachtchenko et al. |
| 2015/0241448 A1 | 8/2015 | Bassaganya-Riera et al. |
| 2016/0115153 A1 | 4/2016 | Bassaganya-Riera et al. |
| 2018/0153898 A1 | 6/2018 | Khleif et al. |

FOREIGN PATENT DOCUMENTS

| | | |
|---|---|---|
| WO | 2012162054 A1 | 11/2012 |
| WO | 2013179264 A2 | 12/2013 |

OTHER PUBLICATIONS

Arora et al., "High Throughput Screen Identifies Small Molecule Inhibitors Specific for Mycobacterium tuberculosis Phosphoserine Phosphatase", J Biol Chem. 289(36): 25149-25165 (2014).
Bell et al., "Targeting RNA-Protein Interactions within the Human Immunodeficiency Virus Type 1 Lifecycle", Biochemistry 52(51): 9269-9274 (2013).
Gautam et al., "Virtual screening of threonine synthase as a target for antimicrobial resistance in Toxoplasma gondii", Elixir Online Journal 9542-9545 (2012).
Jones et al., "Development and validation of a genetic algorithm for flexible docking", Journal of Molecular Biology 267(3): 727-748 (1997).
Khare et al., "Whole-cell screening-based identification of inhibitors against the intraphagosomal survival of Mycobacterium tuberculosis", Antimicrobial Agents and Chemotherapy 57(12): 6372-77 (2013).
Rogers et al., "Novel Cruzain Inhibitors for the Treatment of Chagas Disease", Chem Bio Drug Des. 80(3): 398-405 (2012).
Sandgren et al., "Tuberculosis drug resistance mutation database", PLoS Medicine 6(2): e1000002 pp. 0132-0136 (2009).
Singh et al., "Molecular dynamic simulation and inhibitor prediction of cysteine synthase structured model as a potential drug target for trichomoniasis", BioMed Research International pp. 1-15 (2013).

(Continued)

Primary Examiner — James D. Anderson
(74) Attorney, Agent, or Firm — Nixon Peabody LLP; David S. Resnick; Nicole D. Kling

(57) ABSTRACT

Provided herein are methods and compositions, including synergistic combinations, for the treatment of tuberculosis.

27 Claims, 5 Drawing Sheets

(56) References Cited

OTHER PUBLICATIONS

Ward et al., "Prediction and functional analysis of native disorder in proteins from the three kingdoms of life", Journal of Molecular Biology 337(3): 635-645 (2004).

Werner et al., "Computer-aided identification of novel 3,5-substituted rhodanine derivatives with activity against *Staphylococcus aureus* DNA gyrase", Bioorganic and Medicinal Chemistry 22(7): 2176-87 (2014).

Wolpert et al., "Effects of deletions of mbtH-like genes on clorobiocin biosynthesis in Streptomyces coelicolor", Microbiology 153(5): 1413-1423 (2007).

Akalaeva et al., "In vitro antituberculous, antifungal, and antibacterial activities of 1-phenethylamino-1,2,3,4-tetrahydrocarbazoles", Khimiko-Farmatsevticheskii Zhurnal 24(11): 46-48 (1990).

Akalaeva et al., "Antiviral activity of 1-amino-1,2,3,4-tetrahydrocarbazoles", Khimiko-Farmatsevticheskii Zhurnal 23(3): 299-302 (1989).

Anurag et al., "Unraveling the potential of intrinsically disordered proteins as drug targets: application to Mycobacterium tuberculosis", Molecular Biosystems 5(12): 1752-1757 (2009).

Filitis et al., "Synthesis and in vitro antituberculous activity of alkylaminotetrahydrocarbozoles", Khimiko-Farmatsevticheskii Zhurnal 22: 1217-22 (1988).

Gudmundsson et al., "Substituted tetrahydrocarbazoles with potent activity against human papillomaviruses", Bioorganic & Medicinal Chemistry Letters 19: 3489-3492 (2009).

Micheli et al., "A combinatorial approach to [1,5]benzothiazepine derivatives as potential antibacterial agents", Journal of Combinatorial Chemistry 3: 224-228 (2001).

Eckhouse et al. "Trends in the global funding and activity of cancer research." Molecular oncology 2.1 (2008): 20-32.

Stanley et al. "Identification of novel inhibitors of M. tuberculosis growth using whole cell based high-throughput screening." ACS chemical biology 7.8 (2012): 1377-1384.

METHODS AND COMPOSITIONS FOR THE TREATMENT OF TUBERCULOSIS

CROSS-REFERENCE TO RELATED APPLICATIONS

This application is a 35 U.S.C. § 371 National Phase Entry Application of International Application No. PCT/US2018/049463 filed Sep. 5, 2018, which designates the U.S. and claims benefit under 35 U.S.C. § 119(e) of U.S. Provisional Application No. 62/554,040 filed Sep. 5, 2017, the contents of which are incorporated herein by reference in their entireties.

TECHNICAL FIELD

The technology described herein relates to the treatment of bacterial infections, e.g., *Mycobacterium tuberculosis* (Mtb) infections

BACKGROUND

Tuberculosis (TB) is a pervasive disease estimated to be present in one third of the world's population. While the overall number of TB cases has leveled off due to the effectiveness of antibiotics such as Rifampin and Isoniazid, multiple drug resistant (MDR) and extensively drug resistant (XDR) cases have been on the rise. In particular, drug resistance rates are much higher in developing countries such as China and India, whose healthcare systems are poorly equipped to contain drug resistant strains. An outbreak of drug resistant TB in such regions would be difficult to contain and could reach pandemic levels. In short, new drug choices will be needed to treat today's MDR and XDR-TB.

SUMMARY

Intrinsically Disordered Proteins (IDPs) are structurally flexible proteins that can readily change their shape in order to successfully interact with multiple binding partners. Additionally, IDPs have been hypothesized to play an important role in bacterial drug resistance. As one of the world's most prevalent infectious diseases, *Mycobacterium tuberculosis* (TB) has been observed to have an usually high proportion of IDPs within its proteome. It is also prone to developing multiple drug resistant (MDR) and extensively drug resistant (XDR) strains.

As described herein, the inventors have identified a number of compounds that can inhibit IDPs found in *M. tuberculosis*. These compounds are also capable of inhibiting the growth of both susceptible and MDR TB strains at concentrations comparable to that of Isoniazid and Rifampin.

In one aspect of any of the embodiments, described herein is a method of treating tuberculosis in a subject, the method comprising administering to the subject a composition comprising at least one compound selected from the group consisting of:

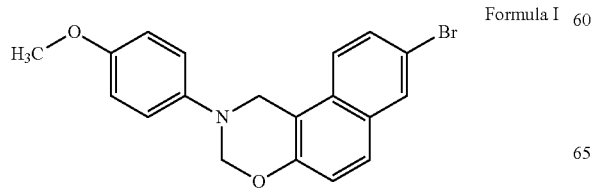

Formula I

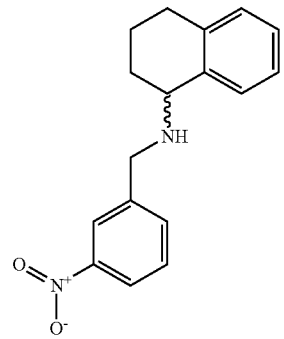

Formula II

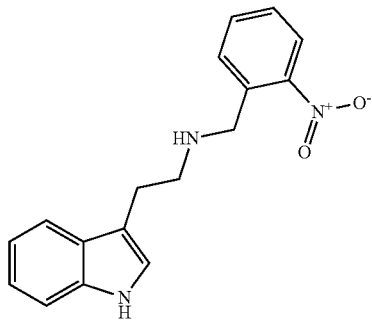

Formula III

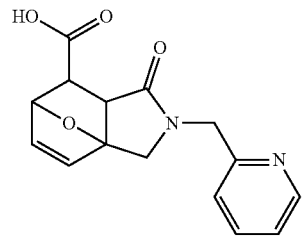

Formula IV

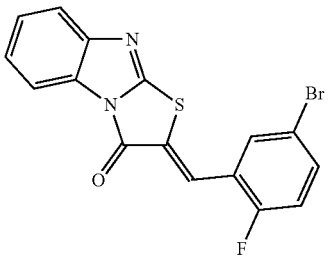

Formula V

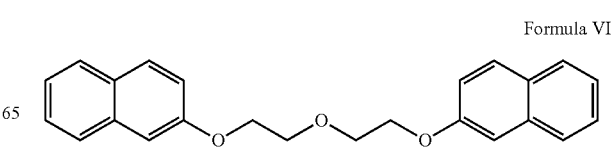

Formula VI

-continued

Formula VII

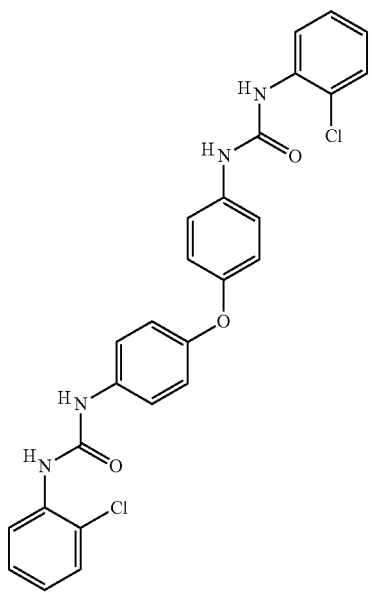

Formula VIII

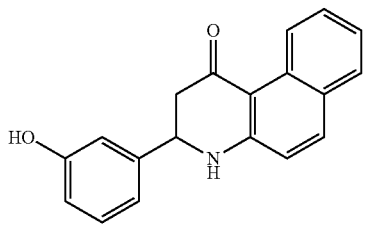

Formula IX

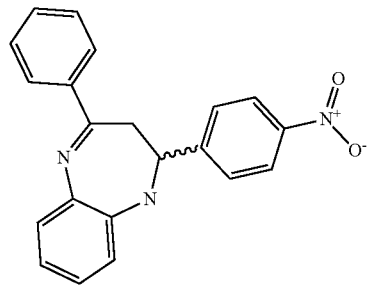

In some embodiments of any of the aspects, the subject is further administered, or the composition further comprises a compound selected from the group consisting of:

Formula X

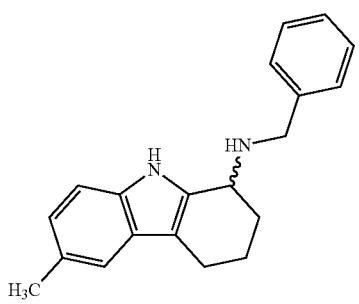

-continued

Formula XI

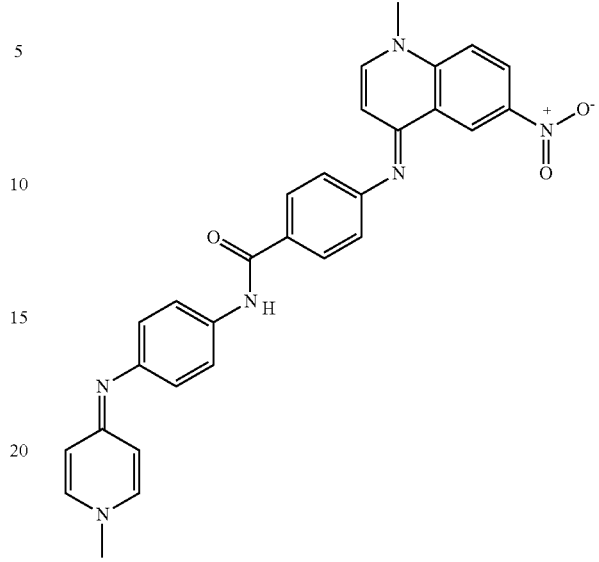

Formula XII

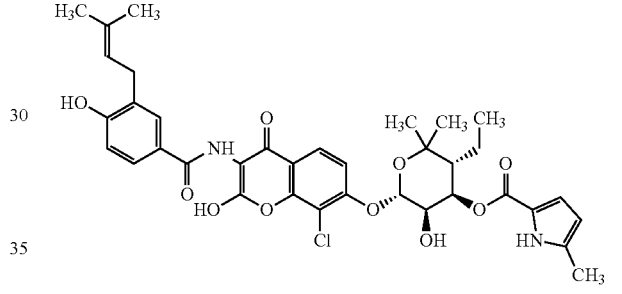

Formula XIII

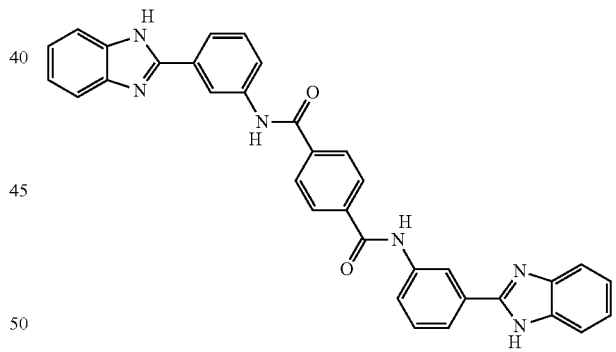

In some embodiments of any of the aspects, the tuberculosis is drug-resistant tuberculosis. In some embodiments of any of the aspects, the tuberculosis is multiple drug-resistant tuberculosis. In some embodiments of any of the aspects, the tuberculosis is extentsively drug-resistant tuberculosis.

In one aspect of any of the embodiments, described herein is a composition for the treatment of tuberculosis, comprising at least one compound selected from the group consisting of Formulas I-IX.

In one aspect of any of the embodiments, described herein is a therapeutically effective amount of at least one compound selected from the group consisting of Formulas I-IX for the treatment of tuberculosis. In one aspect of any of the embodiments, described herein is a therapeutically effective amount of at least two compounds selected from the group consisting of Formulas I-IX for the treatment of tuberculosis. In some embodiments of any of the aspects, the composition further comprises at least one compound selected from the group consisting of Formulas X-XIII.

In one aspect of any of the embodiments, described herein is a composition comprising at least two compounds selected from the group consisting of Formulas I-IX.

In some embodiments of any of the aspects, the composition further comprises at least one compound selected from the group consisting of Formulas X-XIII

BRIEF DESCRIPTION OF THE DRAWINGS

FIG. 3A depicts representative images, FIG. 3B depicts a graph quantifying the results.

DETAILED DESCRIPTION

Figure 1:
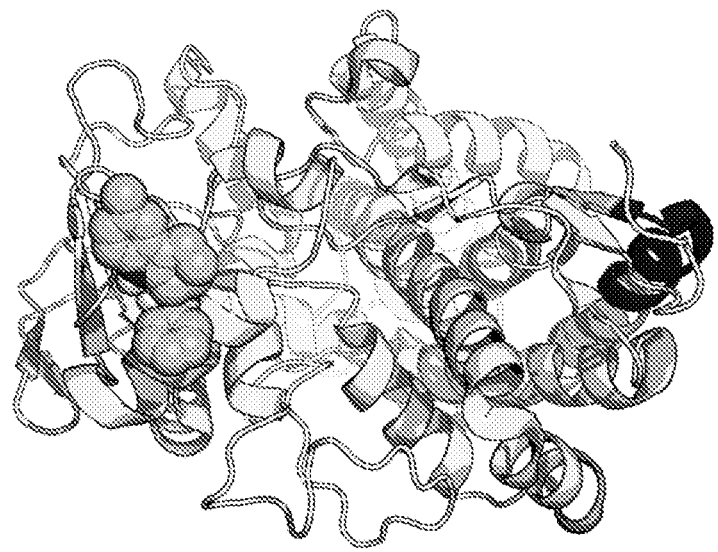
FIG. 1 depicts an illustration of the simulated docking of compound CAS 118498-98-9 with protein PDB 2X5L.
Figure 2:
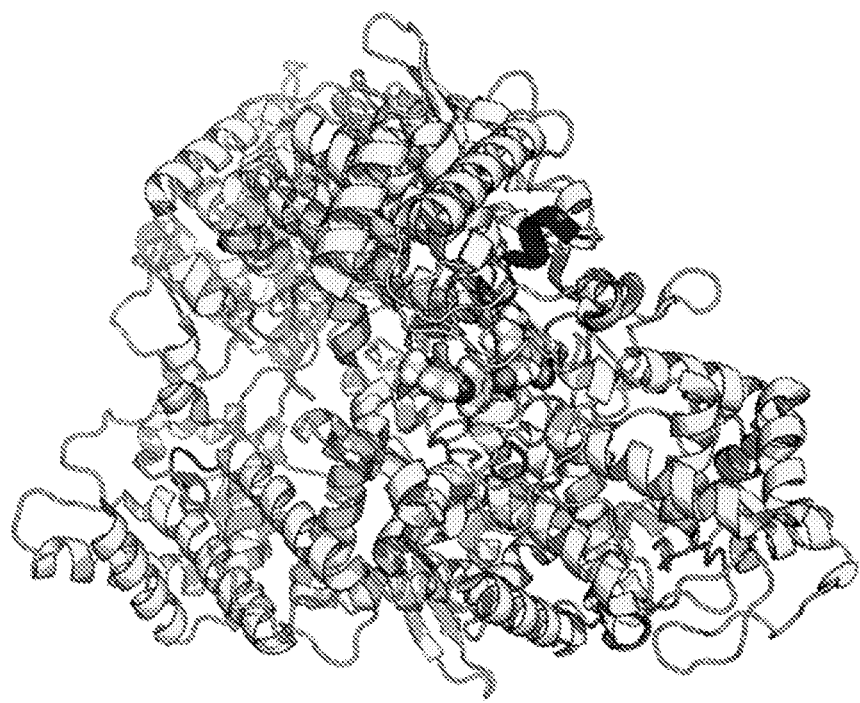
FIG. 2 depicts an illustration of the simulated docking of compound NSC 260594 with TB protein PDB 2CCA.

As described herein, the inventors have identified a number of compounds that demonstrate surprising efficacy in inhibiting the growth of Mycobacteria. Without wishing to be bound by theory, these compounds work, at least in part, by targeting IDPs which are key regulators of drug resistance. As such, Mycobacteria are less likely to develop resistance to the compounds described herein and existing strains of drug-resistant Mycobacteria are susceptible to the presently described compounds.

Described herein are methods and compositions for inhibiting the growth of Mycobacteria and/or treating Mycobacteria infections, e.g., tuberculosis (TB). In some embodiments of any of the aspects, the TB can be drug-resistant TB. In some embodiments of any of the aspects, the TB can be multiple drug-resistant TB (MDR-TB), i.e., a strain of TB which is resistant to at least isoniazid and rifampicin. In some embodiments of any of the aspects, the TB can be extensively drug-resistant TB (XDR-TB), i.e., a strain of TB which is resistant to at least rifampicin, isoniazid, at least one fluoroquinolone, and at least one of amikacin, kanamycin, and capreomycin.

In one aspect of any of the embodiments, described herein is a method of inhibiting the growth of Mycobacteria by contacting the Mycobacteria with one or more of the following compounds. In one aspect of any of the embodiments, described herein is a method of treating a *Mycobacterium* infection, e.g., tuberculosis in a subject, the method comprising administering to the subject a composition comprising at least one compound selected from the group consisting of Formula I (CAS 376374-34-4; 8-bromo-2-(4-methoxyphenyl)-2,3-dihydro-1H-naphtho[1,2-e][1,3]oxazine); Formula II (CAS 353779-33-6; N-(3-nitrobenzyl)-1,2,3,4-tetrahydronaphthalen-1-amine); Formula III (CAS 355816-45-4; 2-(1H-indol-3-yl)-N-(2-nitrobenzyl)ethanamine); Formula IV (CAS 1164528-69-1; (3aS,6R)-1-oxo-2-(pyridin-2-ylmethyl)-1,2,3,6,7,7a-hexahydro-3a,6-epoxyisoindole-7-carboxylic acid); Formula V (CAS 292169-72-3; (Z)-2-(5-Bromo-2-fluorobenzylidene)benzo[4,5]imidazo[2,1-b]thiazol-3(2H)-one); Formula VI (CAS 7151-10-2; NSC 37219; 2-[2-(2-naphthalen-2-yloxyethoxy)ethoxy]naphthalene); Formula VII (NSC 80731; 1-(2-chlorophenyl)-3-[4-[4-[(2-chlorophenyl)carbamoylamino]phenoxy]phenyl]urea); Formula VIII (CAS 333759-52-7; 3-(3-hydroxyphenyl)-3,4-dihydrobenzo[f]quinolin-1(2H)-one); and Formula IX (CAS 60246-87-9; NSC 270738; 2-(4-nitrophenyl)-4-phenyl-2,3-dihydro-1,5-benzothiazepine).

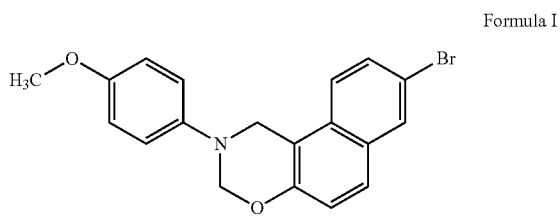

Formula I

Formula II

Formula III

Formula IV

Formula V

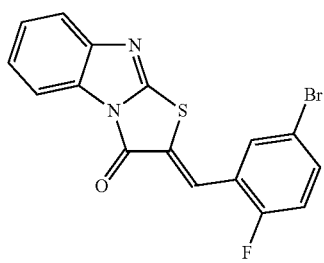

Formula VI

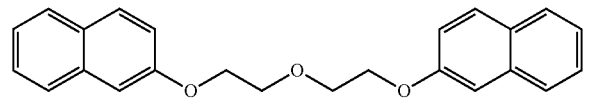

Formula VII

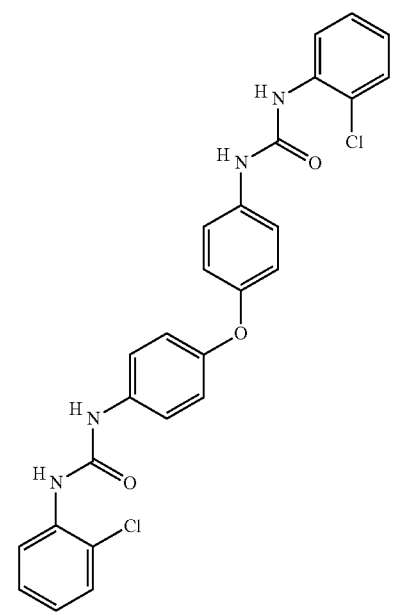

Formula VIII

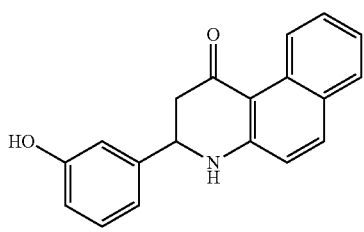

Formula IX

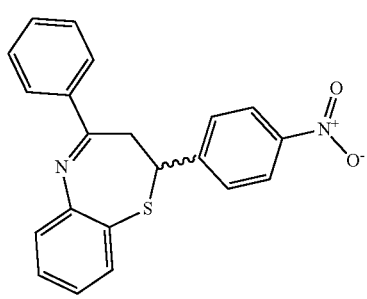

In some embodiments of any of the aspects, a bacterium is contacted with and/or a subject is administered one compound selected from the group consisting of Formulas I-IX. In some embodiments of any of the aspects, a bacterium is contacted with and/or a subject is administered two compounds selected from the group consisting of Formulas I-IX. In some embodiments of any of the aspects, a bacterium is contacted with and/or a subject is administered three compounds selected from the group consisting of Formulas I-IX. In some embodiments of any of the aspects, a bacterium is contacted with and/or a subject is administered four or more compounds selected from the group consisting of Formulas I-IX. In some embodiments of any of the aspects, a bacterium is contacted with and/or a subject is administered five or more compounds selected from the group consisting of Formulas I-IX. In some embodiments of any of the aspects, a bacterium is contacted with and/or a subject is administered six or more compounds selected from the group consisting of Formulas I-IX. In some embodiments of any of the aspects, a bacterium is contacted with and/or a subject is administered seven or more compounds selected from the group consisting of Formulas I-IX. In some embodiments of any of the aspects, a bacterium is contacted with and/or a subject is administered eight or more compounds selected from the group consisting of Formulas I-IX. In some embodiments of any of the aspects, a bacterium is contacted with and/or a subject is administered the compounds of Formulas I-IX. Any combination of the compounds of Formulas I-IX are specifically contemplated. Table 6 presents suitable pairwise combinations of the compounds that are specifically contemplated herein.

TABLE 6

Pairwise combinations of Formulas I-IX for use in the methods and compositions described herein.

| | | Formula: | | | | | | | | |
|---|---|---|---|---|---|---|---|---|---|---|
| | | I | II | III | IV | V | VI | VII | VIII | IX |
| Formula | I |   | X | X | X | X | X | X | X | X |
|   | II | X |   | X | X | X | X | X | X | X |
|   | III | X | X |   | X | X | X | X | X | X |
|   | IV | X | X | X |   | X | X | X | X | X |
|   | V | X | X | X | X |   | X | X | X | X |
|   | VI | X | X | X | X | X |   | X | X | X |
|   | VII | X | X | X | X | X | X |   | X | X |
|   | VIII | X | X | X | X | X | X | X |   | X |
|   | IX | X | X | X | X | X | X | X | X |   |

In some embodiments of any of the aspects, a bacterium contacted with and/or a subject administered at least one compound selected from Formulas I-IX can be further contacted with or administered a compound selected from the group consisting of: Formula X (CAS 118498-98-9; N-benzyl-6-methyl-2,3,4,9-tetrahydro-1H-carbazol-1-amine); Formula XI (NSC260594; 4-[(1-methyl-6-nitroquinolin-4-ylidene)amino]-N-[4-[(1-methylpyridin-4-ylidene) amino]phenyl]benzamide); Formula XII (CAS 39868-96-7; NSC 227186; [(3R,4S,5R,6S)-6-[8-chloro-4-hydroxy-3-[[4-hydroxy-3-(3-methylbut-2-enyl)benzoyl]amino]-2-oxochromen-7-yl]oxy-5-hydroxy-3-methoxy-2,2-dimethyl-oxan-4-yl]5-methyl-1H-pyrrole-2-carboxylate; chlorobiocin); and Formula XIII NSC 61610; 1-N,4-N-bis [3-(1H-benzimidazol-2-yl)phenyl]benzene-1,4-dicarboxamide).

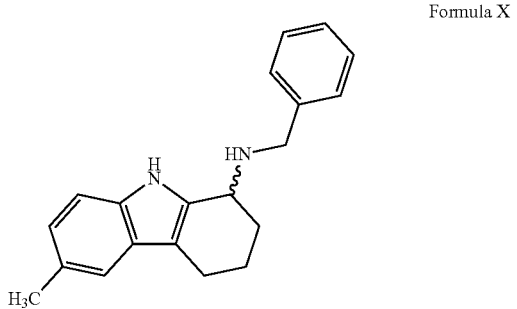

Formula X

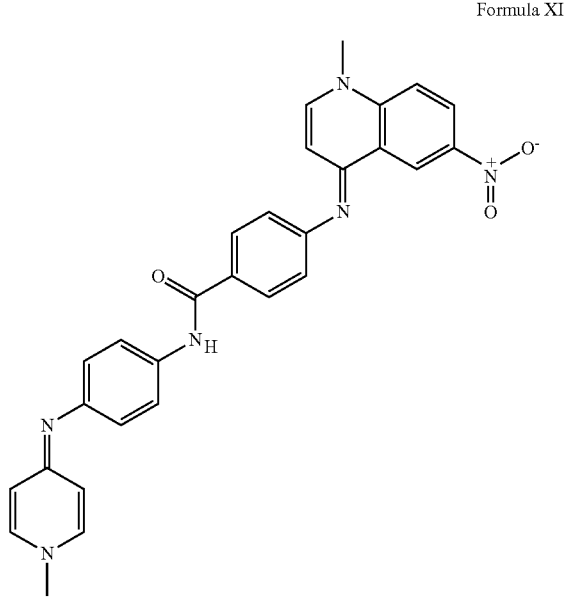

Formula XI

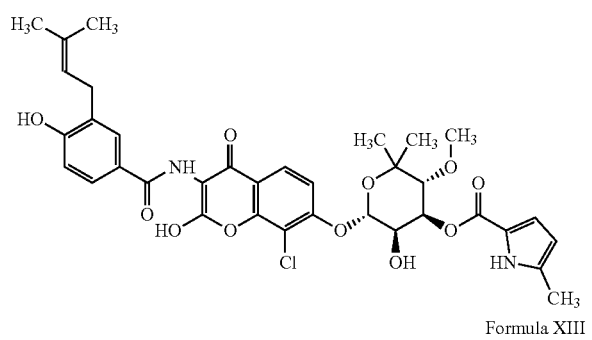

Formula XII

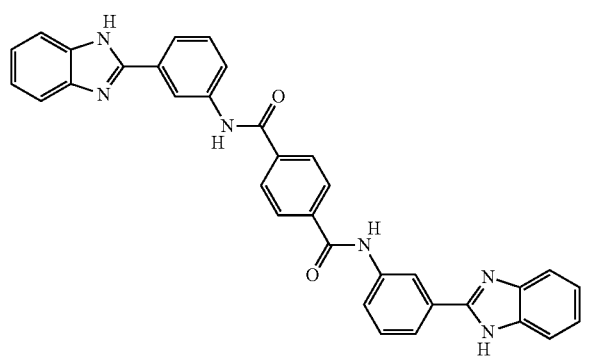

Formula XIII

In one aspect of any of the embodiments, described herein is a composition for inhibiting the growth of a *Mycobacterium* and/or for the treating of a *Mycobacterium* infection, e.g., TB, the composition comprising at least one compound selected from Formulas I-IX. In one aspect of any of the embodiments, described herein is a composition for inhibiting the growth of a *Mycobacterium* and/or for the treating of a *Mycobacterium* infection, e.g., TB, the composition comprising at least two compounds selected from Formulas I-IX. In one aspect of any of the embodiments, described herein is a composition for inhibiting the growth of a *Mycobacterium* and/or for the treating of a *Mycobacterium* infection, e.g., TB, the composition comprising at least three compounds selected from Formulas I-IX. In one aspect of any of the embodiments, described herein is a composition for inhibiting the growth of a *Mycobacterium* and/or for the treating of a *Mycobacterium* infection, e.g., TB, the composition comprising at least four compounds selected from Formulas I-IX. In one aspect of any of the embodiments, described herein is a composition for inhibiting the growth of a *Mycobacterium* and/or for the treating of a *Mycobacterium* infection, e.g., TB, the composition comprising at least five compounds selected from Formulas I-IX. In one aspect of any of the embodiments, described herein is a composition for inhibiting the growth of a *Mycobacterium* and/or for the treating of a *Mycobacterium* infection, e.g., TB, the composition comprising at least six compounds selected from Formulas I-IX. In one aspect of any of the embodiments, described herein is a composition for inhibiting the growth of a *Mycobacterium* and/or for the treating of a *Mycobacterium* infection, e.g., TB, the composition comprising at least seven compounds selected from Formulas I-IX. In one aspect of any of the embodiments, described herein is a composition for inhibiting the growth of a *Mycobacterium* and/or for the treating of a *Mycobacterium* infection, e.g., TB, the composition comprising at least eight compounds selected from Formulas I-IX. In one aspect of any of the embodiments, described herein is a composition for inhibiting the growth of a *Mycobacterium* and/or for the treating of a *Mycobacterium* infection, e.g., TB, the composition comprising the compounds of Formulas I-IX. For illustrative purposes, suitable pairwise combinations of the compounds are shown in Table 6. In one aspect of any of the embodiments, described herein is a therapeutically effective amount of at least one compound selected from Formulas I-IX for the treatment of tuberculosis, e.g., one, two, three, four, five, six, seven, eight, or nine compounds selected from Formulas I-IX.

In one aspect of any of the embodiments, described herein is a composition comprising at least two compounds selected from Formulas I-IX. In one aspect of any of the embodiments, described herein is a composition comprising at least three compounds selected from Formulas I-IX. In one aspect of any of the embodiments, described herein is a composition comprising at least four compounds selected from Formulas I-IX. In one aspect of any of the embodiments, described herein is a composition comprising at least five compounds selected from Formulas I-IX. In one aspect of any of the embodiments, described herein is a composition comprising at least six compounds selected from Formulas I-IX. In one aspect of any of the embodiments, described herein is a composition comprising at least seven compounds selected from Formulas I-IX. In one aspect of any of the embodiments, described herein is a composition comprising at least eight compounds selected from Formulas I-IX. In one aspect of any of the embodiments, described herein is a composition comprising the compounds of Formulas I-IX. For illustrative purposes, suitable pairwise combinations of the compounds are shown in Table 6.

In some embodiments of any of the aspects, the composition can further comprise one or more compounds selected from the group consisting of Formulas X-XIII, e.g, one, two, three, or four of the compounds.

In one aspect of any of the embodiments, described herein is a method of inhibiting the growth of Mycobacteria by contacting the Mycobacteria with one or more of Formulas I-XIII and rifampicin and/or pyrazinamide. In one aspect of any of the embodiments, described herein is a method of treating a *Mycobacterium* infection, e.g., tuberculosis in a subject, the method comprising administering to administering subject a. at least one compound of Formulas I-XIII and b. at least one compound selected from rifampicin and pyrazinamide. Rifampicin and pyrazinamide are known treatments for tuberculosis, and as described in the Examples herein, they can synergize with the compounds of Formulas I-XIII.

In some embodiments of any of the aspects, the a. at least one compound of Formulas I-XIII and b. at least one compound selected from rifampicin and pyrazinamide can be administered separately. In some embodiments of any of the aspects, the a. at least one compound of Formulas I-XIII and b. at least one compound selected from rifampicin and pyrazinamide can be administered sequentially. In some embodiments of any of the aspects, the a. at least one compound of Formulas I-XIII and b. at least one compound selected from rifampicin and pyrazinamide can be administered concurrently. In some embodiments of any of the aspects, the a. at least one compound of Formulas I-XIII and b. at least one compound selected from rifampicin and pyrazinamide can be administered in separate compositions (e.g., two compositions, formulations, solutions, or the like provided in a single kit or package). In some embodiments of any of the aspects, the a. at least one compound of Formulas I-XIII and b. at least one compound selected from rifampicin and pyrazinamide can be administered the same composition.

In one aspect of any of the embodiments, described herein is a. at least one compound of Formulas I-XIII and b. at least one compound selected from rifampicin and pyrazinamide for use in the treatment of tuberculosis.

In some embodiments of any of the aspects, the technology described herein relates to a pharmaceutical composition comprising at least one compound as described herein (e.g., at least one compound of Formulas I-IX and/or at least one of rifampicin and pyrazinamide), and optionally a pharmaceutically acceptable carrier. In some embodiments of any of the aspects, the active ingredients of the pharmaceutical composition comprise at least one compound as described herein (e.g., at least one compound of Formulas I-IX and/or at least one of rifampicin and pyrazinamide). In some embodiments of any of the aspects, the active ingredients of the pharmaceutical composition consist essentially of at least one compound as described herein (e.g., at least one compound of Formulas I-IX and/or at least one of rifampicin and pyrazinamide). In some embodiments of any of the aspects, the active ingredients of the pharmaceutical composition consist of at least one compound as described herein (e.g., at least one compound of Formulas I-IX and/or at least one of rifampicin and pyrazinamide).

In some embodiments of any of the aspects, a pharmaceutical composition comprises at least one compound of Formulas I-IX and/or at least one of rifampicin and pyrazinamide, and optionally a pharmaceutically acceptable carrier. The compositions encompassed by the invention may further comprise at least one pharmaceutically acceptable excipient.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the at least one compound of Formulas I-IX.

Suitable formulations also include aqueous and non-aqueous sterile injection solutions which can contain antioxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS, for example in the range of in one embodiment about 0.1 to 10 mg/ml, in another embodiment about 2.0 mg/ml; and/or mannitol or another sugar, for example in the range of in one embodiment 10 to 100 mg/ml, in another embodiment about 30 mg/ml; phosphate-buffered saline (PBS), and any other formulation agents conventional in the art.

As described in detail below, the pharmaceutical compositions of the present invention comprising at least one compound of Formulas I-IX can be specially formulated for administration to a subject in solid, liquid or gel form. By way of non-limiting example, pharmaceutical compositions can be for use in oral administration. Additionally, the at least one compound of Formulas I-IX can be injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 3,270,960. Examples of dosage forms include, but are not limited to: solutions; gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

In some embodiments of any of the aspects, parenteral dosage forms of at least one compound of Formulas I-IX can also be administered to a subject who is in need of a treatment for an Mtb infection by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration to a patient, including, but not limited to, administration of DUROS®-type dosage forms, and dose-dumping.

Suitable vehicles that can be used to provide parenteral dosage forms of at least one compound of Formulas I-IX as disclosed within are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, the pharmaceutical composition comprising at least one compound of Formulas I-IX as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Sterile compositions for parenteral administration may preferably be aqueous or non-aqueous solutions, suspensions or emulsions. Solvents or vehicles that can be used include water, propylene glycol, a polyethylene glycol, plant oils, in particular olive oil, injectable organic esters, for example ethyl oleate, or other suitable organic solvents. These compositions may also comprise adjuvants, in particular wetting agents, tonicity agents, emulsifiers, dispersants and stabilizers. The sterilization may be performed in several ways, for example by aseptic filtration, by incorporating sterilizing agents into the composition, by irradiation or by heating. They may also be prepared in the form of sterile solid compositions that may be dissolved at the time of use in sterile water or any other injectable sterile medium. The sterile compositions can include sterile aqueous solutions which can also contain buffers, diluents and other suitable additives such as, but not limited to, penetration enhancers, carrier compounds and other pharmaceutically acceptable carriers or excipients. Aqueous suspensions can further contain substances which increase the viscosity of the suspension including, for example, sodium carboxymethylcellulose, sorbitol and/or dextran.

Formulations useful in the methods described herein can also include surfactants. Many organized surfactant structures have been studied and used for the formulation of drugs. Suitable surfactants include fatty acids and/or esters or salts thereof, bile acids and/or salts thereof. In certain embodiments of the invention the surfactant can be anionic, cationic, or nonionic. The use of surfactants in drug products, formulations and in emulsions has been reviewed (Rieger, in Pharmaceutical Dosage Forms, Marcel Dekker, Inc., New York, N.Y., 1988, p. 285).

Vesicles, such as liposomes, have attracted great interest because of their specificity and the duration of action they offer from the standpoint of drug delivery. Liposomes are unilamellar or multilamellar vesicles which have a membrane formed from a lipophilic material and an aqueous interior. The aqueous portion contains the composition to be delivered. Liposomes can be cationic (Wang et al., Biochem. Biophys. Res. Commun., 1987, 147, 980-985), anionic (Zhou et al., Journal of Controlled Release, 1992, 19, 269-274), or nonionic (Hu et al. S. T. P. Pharma. Sci., 1994, 4, 6, 466). Liposomes can comprise a number of different phospholipids, lipids, glycolipids, and/or polymers which can impart specific properties useful in certain applications and which have been described in the art (Allen et al., FEBS Letters, 1987, 223, 42; Wu et al., Cancer Research, 1993, 53, 3765; Papahadjopoulos et al. Ann. N.Y. Acad. Sci., 1987, 507, 64; Gabizon et al. PNAS, 1988, 85, 6949; Klibanov et al. FEBS Lett., 1990, 268, 235; Sunamoto et al. Bull. Chem. Soc. Jpn., 1980, 53, 2778; Illum et al. FEBS Lett., 1984, 167, 79; Blume et al. Biochimica et Biophysica Acta, 1990, 1029, 91; Hughes et al. Methods Mol Biol. 2010; 605:445-59; U.S. Pat. Nos. 4,837,028; 5,543,152; 4,426,330; 4,534,899; 5,013,556; 5,356,633; 5,213,804; 5,225,212; 5,540,935; 5,556,948; 5,264,221; 5,665,710; European Patents EP 0 445 131 B1; EP 0 496 813 B1; and European Patent Publications WO 88/04924; WO 97/13499; WO 90/04384; WO 91/05545; WO 94/20073; WO 96/10391; WO 96/40062; WO 97/0478).

The compositions of the present invention can be prepared and formulated as emulsions or microemulsions. Emulsions are typically heterogeneous systems of one liquid dispersed in another in the form of droplets usually exceeding 0.1 μm in diameter and have been described in the art. Microemulsion can be defined as a system of water, oil and amphiphile which is a single optically isotropic and thermodynamically stable liquid solution and can comprise surfactants and cosurfactants. Both of these drug delivery means have been described in the art (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 199, 245, & 335; Higuchi et al., in Remington's Pharmaceutical Sciences, Mack Publishing Co., Easton, Pa., 1985, p. 301; Leung and Shah, in: Controlled Release of Drugs: Polymers and Aggregate Systems, Rosoff, M., Ed., 1989, VCH Publishers, New York, pages 185-215; Schott, in Remington's Pharmaceutical Sciences, Mack Publishing Co., Easton, Pa., 1985, p. 271; Constantinides et al., Pharmaceutical Research, 1994, 11, 1385-1390; Ritschel, Meth. Find. Exp. Clin. Pharmacol., 1993, 13, 205; Ho et al., J. Pharm. Sci., 1996, 85, 138-143; Lee et al., Critical Reviews in Therapeutic Drug Carrier Systems, 1991, p. 92; U.S. Pat. Nos. 6,191,105; 7,063,860; 7,070,802; 7,157,099).

Compounds that alter or modify the solubility of a pharmaceutically acceptable salt of at least one compound of Formulas I-IX as disclosed herein can also be incorporated into the parenteral dosage forms of the disclosure, including conventional and controlled-release parenteral dosage forms. Such formulations can comprise a controlled-dosage form of at least one compound of Formulas I-IX, e.g. a biodegradable hydrogel comprising at least one compound of Formulas I-IX.

Pharmaceutical compositions comprising at least one compound of Formulas I-IX can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethyl-ammonio-1-propanesulfonate), Big-CHAPS (N, N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate. Oral formulations and their preparation are described in detail in U.S. Pat. No. 6,887,906, US Publn. No. 20030027780, and U.S. Pat. No. 6,747,014, each of which is incorporated herein by reference.

The oral formulations of the agents described herein, e.g. at least one compound of Formulas I-IX, further encompass, In some embodiments of any of the aspects, anhydrous pharmaceutical compositions and dosage forms comprising the agents as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

The at least one compound of Formulas I-IX as described herein can be administered directly to the airways in the form of an aerosol or by nebulization. Therapeutic agents can be administered as aerosols, packaged in a pressurized aerosol container together with suitable propellants, for example, hydrocarbon propellants like propane, butane, or isobutane with conventional adjuvants. In other embodiments, the agent can be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means, including by using many nebulizers known and marketed today. As is well known, any suitable gas can be used to apply pressure during the nebulization, with preferred gases being those which are chemically inert to the therapeutic agent. Exemplary gases include, but are not limited to, nitrogen, argon or helium.

In some embodiments of any of the aspects, a therapeutic agent can be administered directly to the airways in the form of a dry powder by use of an inhaler. Exemplary inhalers include metered dose inhalers and dry powdered inhalers. Suitable powder compositions include, by way of illustration, powdered preparations of a therapeutic agent as described herein thoroughly intermixed with lactose, or other inert powders acceptable for, e.g., intrabronchial administration. The powder compositions can be administered via an aerosol dispenser or encased in a breakable capsule which may be inserted by the subject into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

In some embodiments of any of the aspects, at least one compound of Formulas I-IX can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

Certain aspects of the invention described herein relate to administering a compound(s) described herein to a patient in need of a treatment for an *Mycobacterium* infection, e.g., a Mtb infection. In some embodiments of any of the aspects, the invention comprises first diagnosing the subject, such as a human patient, as having an Mtb infection or suffering from the symptoms of an Mtb infection.

Subjects having tuberculosis (e.g., an Mtb infection) or suffering from the symptoms of an Mtb infection can be identified by a physician using current methods of diagnosing Mtb infections. Symptoms and/or complications of Mtb infection useful in making such diagnoses include, but are not limited to chronic cough, blood-tinged sputum, fever, chest pain, pallor, chills, fatigue, night sweats, and weight loss. If Mtb infection spreads to organs other than the lungs, a variety of symptoms can arise that are specific to the particular organ infected. Test and diagnostic tools that may aid in a diagnosis of Mtb infection include, but are not limited to x-rays, chest x-rays, tuberculin skin test, blood tests, microscopic examination of bodily fluids, microbiological culture of bodily fluids, chest photofluorography, the Ziehl-Neelsen stain, auramine-rhodamine stain, fluorescent microscopy, PCR tests, amplified *Mycobacterium tuberculosis* direct test (MTD, Gen-Probe) or an interferon gamma release assay (IGRA).

Subjects can have an elevated risk of having or developing an Mtb infection for a number of reasons. Risk factors that predispose a subject to Mtb include, but are not limited to, certain polymorphisms in the IL12B gene, a family history of Mtb infection, treatment with immunosuppressive drugs, cigarette use, treatment for rheumatoid arthritis with anti-TNFα therapy, illegal drug use, low BMI, AIDS, silicosis, exposure to silica particles, diabetes mellitus, jejunoilelal bypass, renal and cardiac transplantation, carcinoma of the head or neck, other neoplasms and incarceration in a prison.

Suitable methods for administration of a composition or compound of the present invention include but are not limited to intramuscular, intravenous, inhalation, intranasal, intravesicular, intraarticular, intralesional, peritoneal, subcutaneous, topical, or oral administration. In one embodiment of the methods described herein, the composition or compound is administered orally. In one embodiment of the methods described herein, the composition or compound is administered intravenously.

In some embodiments of any of the aspects, the composition or compound described herein is administered to a subject to whom another antibiotic or TB treatment is also being administered. In some embodiments of any of the aspects, the composition or compound described herein and the other antibiotic or treatment are administered concurrently. In some embodiments of any of the aspects, the composition or compound described herein and the other antibiotic or treatment are administered sequentially. The method of combining administration of a composition or compound described herein and another antibiotic or treatment can be based upon factors such as desired routes of administration, dosages desired, type of antibiotics, severity of the infection, the patient's responsiveness to treatment and other parameters that are assessed by one of ordinary skill in the art in selecting a course of treatment for a particular subject.

Current treatment standards for Mtb infection include a 6 month treatment using the WHO recommended treatment regimen (DOTS, Directly Observed Treatment, Short-course), which consists of 4 drugs isoniazid, rifampacin, pyrazinamide and ethambutol used in combination (WHO Report on the Tuberculosis Epidemic, 2000) over a course of 6 months. In some embodiments of any of the aspects, a composition or compound described herein can be administered to a patient in addition to isoniazid, rifampacin, pyrzainamide, and ethambutol or in place of one of these antibiotics.

In some embodiments of any of the aspects, a subject administered a composition or compound(s) described herein can be administered additional agents to treat Mtb infections and/or symptoms and complications of an Mtb infection. In some embodiments of any of the aspects, the pharmaceutical composition comprising a compound(s) described herein comprises additional agents to treat Mtb infections and/or symptoms and complications of an Mtb infection. By way of example, in the case of a subject with an Mtb infection, antibiotics can be administered to treat the infection and administration of steroids or nutritional supplements can also be useful. Antibiotics used to treat an Mtb infection include, but are not limited to rifampicin, isoniazid, aminoglycosides (i.e. amikacin or kanamycin), polypeptides (i.e. capreomycin), fluoroquinolones, (moxifloxacin or ciprofloxacin), thioamides (i.e. ethionamide or prothionamide), cycloserine, and para-aminosalicylic acid. Steroids are typically administered to patients with tuberculosis meningitis and tuberculosis pericarditis. Examples of steroids include, but are not limited to, prednisone and dexamethasone. Nutritional supplements can include, but are not limited to arginine and Vitamin D. Surgery is also a treatment option for Mtb infections. Surgeries can include, but are not limited to lobectomy and pneumonectomy.

In certain embodiments, an effective dose of a composition comprising at least one compound of Formulas I-IX as described herein can be administered to a patient once. In certain embodiments, an effective dose of a composition comprising at least one compound of Formulas I-IX can be administered to a patient repeatedly. For systemic administration, subjects can be administered a therapeutic amount of a composition comprising at least one compound of Formulas I-IX, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. Mtb growth and/or levels by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising at least one compound of Formulas I-IX can be administered over a period of time, such as over a 5 minute, 10 minute, 15 minute, 20 minute, or 25 minute period.

The dosage ranges for the administration of at least one compound of Formulas I-IX, according to the methods described herein depend upon, for example, the form of the compound, its potency, and the extent to which symptoms, markers, or indicators of a condition described herein are desired to be reduced, for example the percentage reduction desired for Mtb growth. The dosage should not be so large as to cause adverse side effects. Generally, the dosage will vary with the age, condition, and sex of the patient and can be determined by one of skill in the art. The dosage can also be adjusted by the individual physician in the event of any complication.

The compositions and methods described herein can be administered to a subject having or diagnosed as having tuberculosis. In some embodiments of any of the aspects, the methods described herein comprise administering an effective amount of compositions described herein, e.g. a compound of Formula I-IX to a subject in order to alleviate a symptom of tuberculosis. As used herein, "alleviating a symptom of tuberculosis" is ameliorating any condition or symptom associated with the tuberculosis. As compared with an equivalent untreated control, such reduction is by at least 5%, 10%, 20%, 40%, 50%, 60%, 80%, 90%, 95%, 99% or more as measured by any standard technique.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a compound that is sufficient to provide a particular anti-Mtb effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation. Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, severity of infection and the physical condition and prior medical history of the subject being treated. Determination and adjustment of a therapeutically effective dose, as well as evaluation of when and how to make such adjustments, are known to those of ordinary skill in the art of medicine.

In one embodiment of the methods described herein, a minimally therapeutic dose is administered. The term "minimally therapeutic dose" refers to the smallest dose, or smallest range of doses, determined to be a therapeutically effective amount as that term is used herein.

The efficacy of a compound in, e.g. the treatment of a condition described herein, or to induce a response as described herein (e.g. decrease in the growth and/or level of Mtb) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for growth and/or numbers of Mtb, among others. The dosage can be determined by a physician and adjusted, as necessary, to suit observed effects of the treatment.

Efficacy of treatment can be assessed, for example by measuring a marker, indicator, symptom or incidence of a Mtb infection as described herein or any other measurable parameter appropriate, e.g. coughing, fatigue, etc. The Mtb infection can also be examined by, for example, x-ray or IGRA. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. Mtb levels). It is well within the ability of one skilled in the art to monitor efficacy of administration and/or treatment by measuring any one of such parameters, or any combination of parameters. Efficacy for a given compound (s) described herein or formulation of that drug can also be judged using an experimental animal model known in the art for a condition described herein. When using an experimental animal model, efficacy of treatment is evidenced when a statistically significant change in a marker is observed, e.g. the extent of the Mtb infection or mortality.

In vitro and animal model assays are provided herein which allow the assessment of a given dose of a compound. By way of non-limiting example, the effects of a dose of a compound of Formulas I-IX can be assessed by determining the MIC of the compound against one or more strains of Mtb in vitro.

The efficacy of a given dosage combination can also be assessed in an animal model, e.g. a mouse model of Mtb infection.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a staticaly significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of tuberculosis. A subject can be male or female.

A subject can be one who has been previously diagnosed with or identified as suffering from or having a condition in need of treatment (e.g. tuberculosis) or one or more complications related to such a condition, and optionally, have already undergone treatment for tuberculosis or the one or more complications related to tuberculosis. Alternatively, a subject can also be one who has not been previously diagnosed as having tuberculosis or one or more complications related to tuberculosis. For example, a subject can be one who exhibits one or more risk factors for tuberculosis or one or more complications related to tuberculosis or a subject who does not exhibit risk factors.

A "subject in need" of treatment for a particular condition can be a subject having that condition, diagnosed as having that condition, or at risk of developing that condition.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. tuberculosis. The term "treating" includes reducing or alleviating at least one adverse effect or symptom of a condition, disease or disorder associated with tuberculosis. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating tuberculosis in a subject, the method comprising administering to the subject a composition comprising at least one compound selected from the group consisting of:

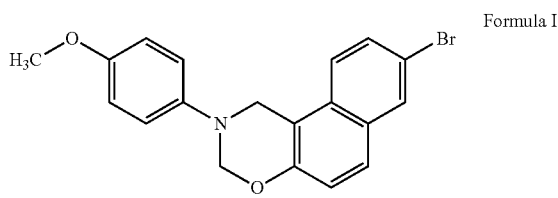

Formula I

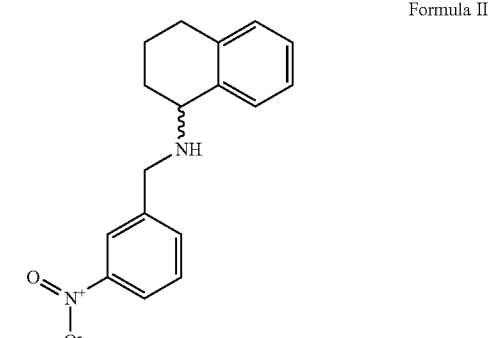

Formula II

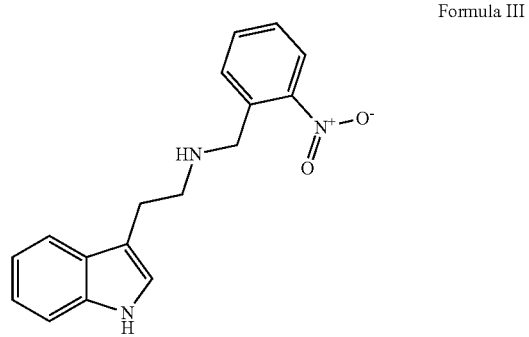

Formula III

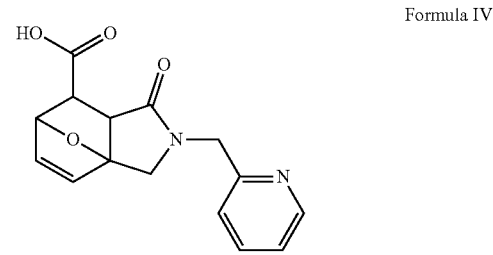

Formula IV

-continued

Formula V
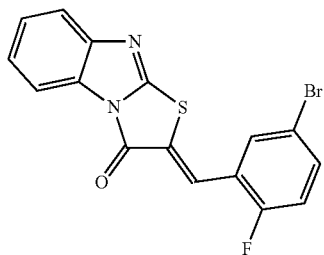

Formula VI
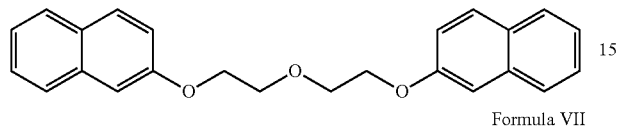

Formula VII
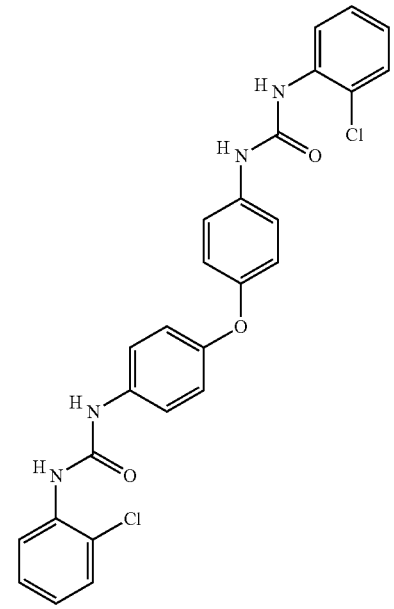

Formula VIII

Formula IX
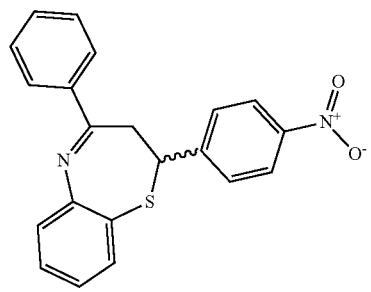

Formula X
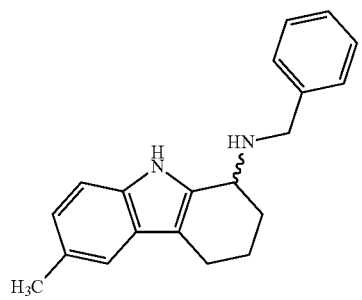

Formula XI

Formula XII
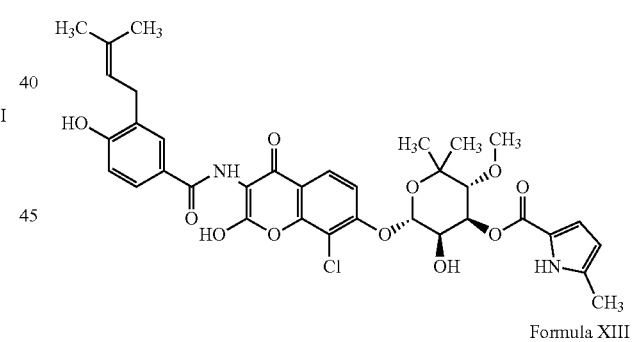

Formula XIII

2. The method of paragraph 1, wherein the subject is further administered, or the composition further comprises a compound selected from the group consisting of:

3. The method of any of paragraphs 1-2, wherein the tuberculosis is drug-resistant tuberculosis.

4. The method of paragraph 3, wherein the tuberculosis is multiple drug-resistant tuberculosis.
5. The method of paragraph 3, wherein the tuberculosis is extentsively drug-resistant tuberculosis.
6. A composition for the treatment of tuberculosis, comprising at least one compound selected from the group consisting of Formulas I-IX.
7. A therapeutically effective amount of at least one compound selected from the group consisting of Formulas I-IX for the treatment of tuberculosis.
8. A composition comprising at least two compounds selected from the group consisting of Formulas I-IX.
9. The composition of any of any of paragraphs 6-8, further comprising at least one compound selected from the group consisting of Formulas X-XIII.

Some embodiments of the technology described herein can be defined according to any of the following numbered paragraphs:

1. A method of treating tuberculosis in a subject, the method comprising administering to the subject a composition comprising at least one compound selected from the group consisting of:

Formula I
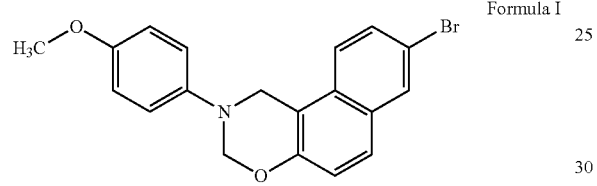

Formula II
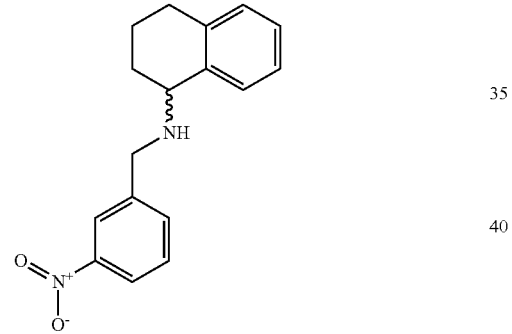

Formula III
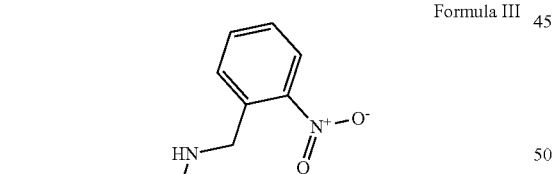

Formula IV
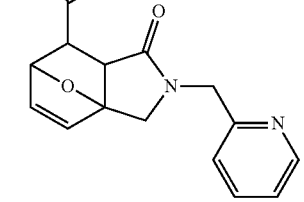

Formula V
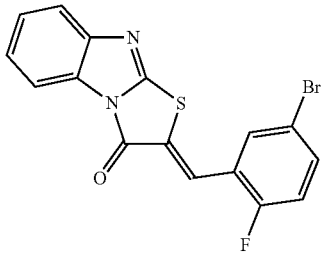

Formula VI

Formula VII
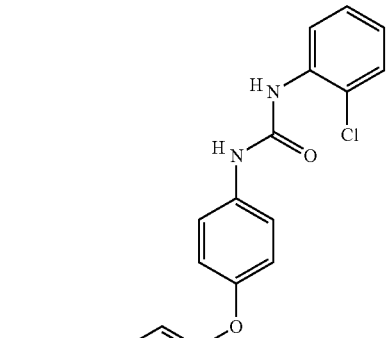

Formula VIII
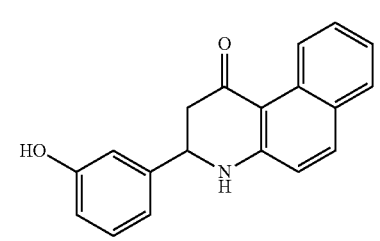

Formula IX
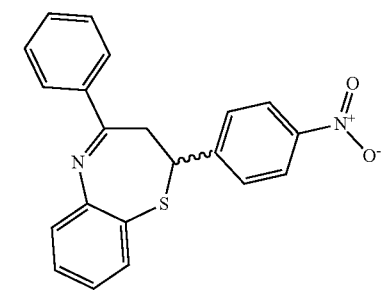

2. The method of paragraph 1, wherein the subject is further administered, or the composition further comprises a compound selected from the group consisting of:

Formula X

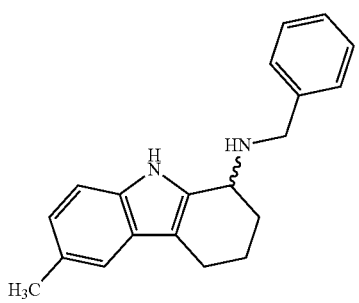

Formula XI

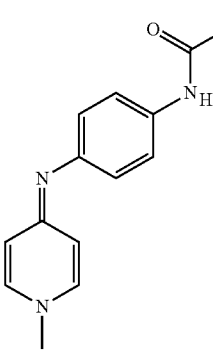

Formula XII

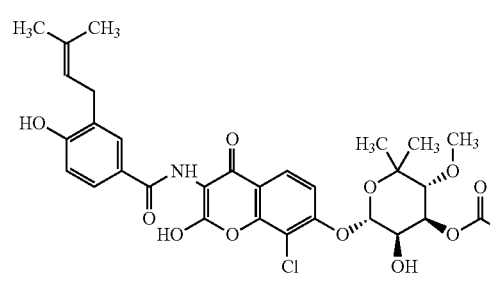

Formula XIII

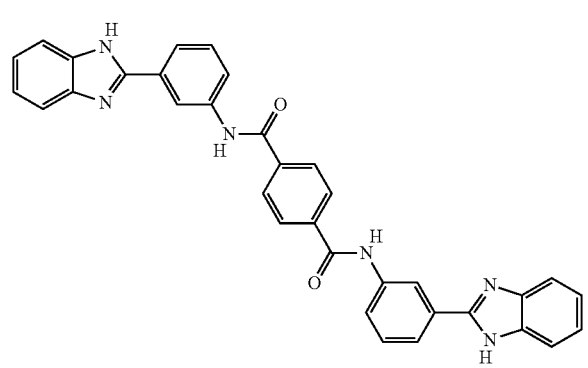

3. The method of any of paragraphs 1-2, wherein the tuberculosis is drug-resistant tuberculosis.

4. The method of paragraph 3, wherein the tuberculosis is multiple drug-resistant tuberculosis.

5. The method of paragraph 3, wherein the tuberculosis is extentsively drug-resistant tuberculosis.

6. A composition for the treatment of tuberculosis, comprising at least one compound selected from the group consisting of Formulas I-IX.

7. A therapeutically effective amount of at least one compound selected from the group consisting of Formulas I-IX for the treatment of tuberculosis.

8. A composition comprising at least two compounds selected from the group consisting of Formulas I-IX.

9. The composition of any of any of paragraphs 6-8, further comprising at least one compound selected from the group consisting of Formulas X-XIII.

10. A method of treating tuberculosis in a subject, the method comprising administering to the subject
 a. at least one compound selected from the group consisting of:

Formula I

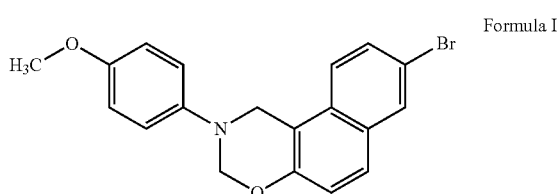

Formula II

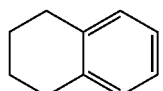

Formula III

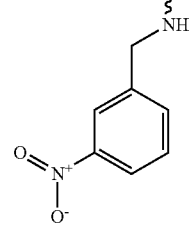

Formula IV

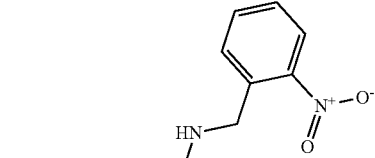

Formula V
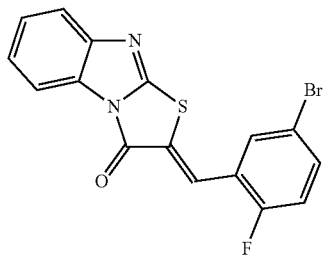
Formula VI
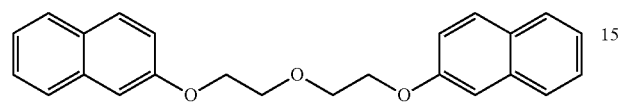
Formula VII
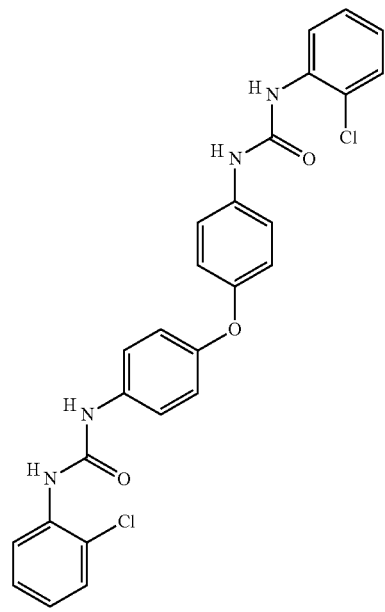
Formula VIII
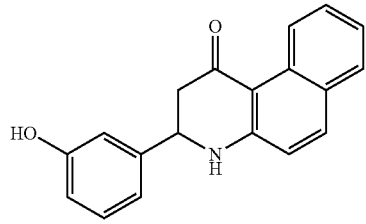
Formula IX
Formula X
Formula XI
Formula XII
Formula XIII
and
b. at least one compound selected from the group consisting of rifampicin or pyrazinamide.

11. The method of paragraph 10, wherein the tuberculosis is drug-resistant tuberculosis.
12. The method of paragraph 11, wherein the tuberculosis is multiple drug-resistant tuberculosis.
13. The method of paragraph 11, wherein the tuberculosis is extentsively drug-resistant tuberculosis.
14. The method of any of paragraphs 10-13, wherein the compounds of are administered separately.
15. The method of any of paragraphs 10-13, wherein the compound of are administered concurrently.
16. A compound selected from the group consisting of Formulas I-XIII and a compound selected from the group consisting of rifampicin and pyrazinamide for the treatment of tuberculosis.
17. The compounds of paragraph 16, wherein the tuberculosis is drug-resistant tuberculosis.
18. The compounds of paragraph 17, wherein the tuberculosis is multiple drug-resistant tuberculosis.
19. The compounds of paragraph 17, wherein the tuberculosis is extentsively drug-resistant tuberculosis.
20. The compounds of any of paragraphs 16-19, wherein the compounds of are in separate formulations or compositions.
21. The compound of any of paragraphs 16-19, wherein the compound of are in the same formulation or composition.

EXAMPLES

Example 1: In Silico Screening of Disordered Proteins for Drug-Resistant Tuberculosis Compound Discovery Recent research has shown the importance of Intrinsically Disordered Proteins (IDPs) in many biological pathways[1]. Most notably, due to their ability to conform to multiple binding partners, IDPs have been hypothesized to play an important role in bacterial drug resistance. As one of the world's most prevalent infectious diseases, *Mycobacterium tuberculosis* (TB) has been observed to have an usually high proportion of IDPs within its proteome. It is also prone to develop multiple drug resistant (MDR) and extensively drug resistant (TB) strains[3]. Demonstrated herein is a significant statistical association between drug resistance and protein disorder within the TB proteome. In comparison with the TB proteome, drug resistance related proteins contain a much higher proportion of both disordered proteins and total disordered regions ($p<1.349*10^{-10}$, $p<5.559*10^{-7}$ respectively). Using this finding, target proteins containing disordered regions in close proximity to residues modified by drug resistance Single Nucleotide Polymorphisms (SNPs) were identified for TB drug development. In silico drug screening process discovered compounds capable of inhibiting both susceptible and MDR TB strains at concentrations comparable to that of Isoniazid and Rifampin[4]. The results presented herein confirm the biological importance of IDPs in bacterial drug resistance and identify several drug molecules to treat MDR/XDR-TB.

Intrinsically Disordered Proteins (IDPs) are flexible proteins lacking a well-defined tertiary structure. Contrary to the long-held paradigm that unique protein structures imply function[5], IDPs are able to fold into multiple conformations, allowing them to have a greater range of binding partners[6]. As a result of this flexibility, IDPs often act as central hubs in protein interaction networks and are predicted to play crucial roles in many biological pathways[1]. Due to their inability to be visualized through conventional crystallography methods, IDPs have remained relatively unstudied until the past decade[7]. However, due to their characteristics, IDPs are hypothesized to be crucial in the evolution of drug resistance in problematic microorganisms[2]. A compelling test for this hypothesis would be *Mycobacterium tuberculosis*, whose proteome contains an abnormally high proportion of IDPs compared to other bacterium[3].

Tuberculosis is a pervasive disease estimated to be present in one third of the world's population[8]. While the overall number of TB cases has leveled off due to the effectiveness of antibiotics such as Rifampin and Isoniazid, multiple drug resistant (MDR) and extensively drug resistant (XDR) cases have been on the rise[9]. In particular, drug resistance rates are much higher in developing countries such as China and India, whose healthcare systems are poorly equipped to contain drug resistant strains[10]. An outbreak of drug resistant TB in such regions would be difficult to contain and could reach pandemic levels[11]. In short, new drug choices will be needed to treat today's MDR and XDR-TB.

Described herein is a combination of large-scale analysis of TB protein structures and gene functions to map TB genetic variants to their respective protein residues[12,13]. This confirmed the importance of IDPs in TB drug resistance and to discover high profile IDPs containing disordered regions affected by drug resistance SNPs. Such target proteins can play central roles in protein interaction networks which allow for the evolution of drug resistance. Therefore, compounds designed to target these proteins permit effective treatment of MDR and XDR TB.

Methods

TB drug resistance data for both genes and SNPs was obtained from the Tuberculosis Drug Resistance Mutation Database[13]. This information was subsequently mapped to their respective proteins and residues through the NCBI gene, protein, and SNP databases. Information about the overall TB proteome was obtained through Protein Data Bank[14]. The frequency of disordered proteins and regions across these two populations were determined using the DisEMBL predictor and by locating missing residues in the PDB crystallography data[15]. Statistical analysis was performed on the frequency of disorder across these two datasets.

In silico screening was performed using a flexible docking algorithm on the PubChem building blocks compound library, and top compounds were selected based on their predicted binding affinities[4]. Biological validation of the inhibitory properties of identified compounds was initially performed on the *Bacillus* Calmette-Guérin (BCG) *Mycobacterium bovis* strain, and high-performing compounds were subsequently tested on both drug resistant and susceptible *Mycobacterium tuberculosis* strains. The test strains were transformed with green fluorescent protein to measure growth concentrations after incubation to determine minimum inhibitory concentration (MIC).

Statistical Analysis. A comprehensive list of currently identified TB proteins was obtained from Protein Data Bank (PDB)[18] and the National Center of Biotechnology Information (NCBI) protein database. For proteins with empirically validated structures obtained through either x-ray crystallography or nuclear magnetic resonance (NMR) experiments, disordered regions were identified by cross referencing locations of missing coordinates with known primary amino acid sequences. Since x-ray crystallography and NMR experiments are unable to display disordered residues, proteins with missing coordinates are likely to be IDPs. For proteins without known structures, an artificial neural network based predictor (DisEMBL)[19] was used to predict the existence and locations of disordered regions. The stringent Remark-465 definition based off of x-ray crystallography data was used for consistency with empirical results.

A collection of known TB drug resistance SNPs were obtained from the TB Drug Resistance Mutation Database (TBDReaMDB)[13]. These SNP locations were then mapped to their respective protein residues through first locating the respective gene coordinates of each SNP via the NCBI gene database, and then identifying their affected protein residue through the NCBI protein database. The occurrence of IDPs in the drug resistance related dataset was then compared to overall IDP frequency in the population using the Fisher Exact Test (n=797). In addition, the occurrence of drug resistance related SNPs in ordered and disordered regions was also compared to the overall occurrence of SNPs in ordered and disordered regions (n=537472). Proteins identified with drug-resistance related SNPs located within disordered regions were then used in docking experiments to identify potential binding candidates.

GOLD Docking. GOLD 5.1 (Genetic Optimization for Ligand Docking)[5] from Cambridge Crystallographic Data Center, UK was applied in the virtual screening. GOLD allows for docking flexible ligands into a protein binding site. GOLD has been tested on a large number of complexes extracted from the Protein Data Bank. The overall conclusion of these tests was that the top-ranked GOLD solution was correct in 70%-80% of cases. The scoring functions for docking offered in GOLD include Goldscore[20], Chemscore[21], ASP (Astex Statistical Potential)[22] and PLP (Piecewise Linear Potential)[23]. GOLD uses a genetic algorithm (GA) to search favorable ligand poses. A population of chromosomes is manipulated during a GA run, with each chromosome representing a trial docking. A chromosome contains all the information needed to completely define a trial ligand pose and is associated with a fitness value, computed from the scoring function2[4]. Different values of the genetic algorithm parameters may be used to control the balance between the speed of GOLD and the reliability of its predictions. GOLD investigates the full range conformational flexibility of ligand with partial flexibility of the receptor.

Receptor coordinates of each PDB crystal structure of *Mycobacterium tuberculosis* protein was used to define the binding site for docking simulations. In each docking simulation, the alternate conformations, all the solvent molecules were removed from the crystal structures and hydrogen atoms were added to the whole protein. The ligand binding site for docking simulation was defined from the protein regions that are predicted as disordered. The list of residues in the disordered regions was specified in a file. The ligand dataset provided to GOLD for docking was the National Cancer Institute (NCI) Diversity Set III which contains 1880 ZINC molecules in SDF format. Top 50 ligands with the best fitness scores among all the docked solutions were kept at the end of a docking run. The steric complementarily between a receptor and a ligand was estimated via PLP implemented in GOLD. The total PLP, which is represented as "Fitness", consists of the heavy-atom clash potential and the torsional potential used within Chemscore. In addition, PLP is capable of considering covalent docking, flexible side-chains and handling constraints. To allow poor hydrogen bonds to occur at the beginning of a GA run, the distance between donor hydrogen and fitting point is less than 2.0Å for the bond to count towards the fitness score. At the start of the run, to allow a few bad bumps to be tolerated, 10Å is set as the cut off value for external van der Waals (vdw) energies. In the docking simulation, protein flexibility is handed by allowing side chains to rotate within defined bounds in GOLD. GOLD uses a rotamer library described in Lovell et al, 2000[25]. This is a compilation of the most commonly observed side-chain conformations for the naturally occurring amino acids. Up to 10 residues in the disordered region were specified with rotatable side chains. One rotamer conformation is allowed for the side chain. All other parameters were remained at their default values.

An alternative docking approach, ensemble docking, is applied to address protein flexibility for the disordered regions which are absent in the protein crystal structure. Five conformations of the protein regions were generated via the protocol "Loop Refinement (MODELLER)" in Discovery Studio 2.5, in which, the missing disordered region is built and treated as a loop in the crystal structure and followed by refinement through MODELLER. The binding site was defined using the best conformation from MODELLER as a reference. Binding sphere was defined using disordered region with a radius of 10Å. Active atoms included those belong to the residues in and near the disordered region. Each ligand was then docked into the multiple (maximum 20) conformations of the same protein in a single run. GOLD selects the best protein for a particular ligand based on the maximum fitness value of a ligand. The ensemble docking applied in this project is a test run to demonstrate a way to deal with large backbone movement of disordered proteins in docking. Since the conformational space of disordered proteins is enormous, a large set of conformations is required to perform the ensemble docking. Besides the big ligand dataset, a large structural ensemble of proteins adds exponential computation cost in the docking. Therefore, in this project, protein flexibility is mainly addressed by considering side-chain flexibility of a disordered protein region present in a crystal structure.

Anti-BCG and MTB assays. The BCG and MTB H37Rv strains used here were transformed with green fluorescent protein (GFP) constitutive expression plasmid pUV3583c with direct readout of fluorescence as a measure of bacterial growth. BCG and MTB H37Rv were grown at 37° C. to mid log phase in Middlebrook 7H9 broth (Becton Dickinson) supplemented with 10% OADC enrichment (Becton Dickinson) 0.05% tween-80, and 0.2% glycerol. The culture was then diluted with culture medium to a bacterial suspension with OD600 values of 0.025. Aliquots (78 μL) of the bacterial suspension were added to each well of the flat-bottom 96-well microplates, followed by adding 2 μL compounds (in DMSO). The compounds were serially two-fold diluted in each column. Isoniazid (concentration from 200-1.56 ng/ml) served as positive control and DMSO as negative control. The plate was incubated at 37° C. for 3 days for BCG or 10 days for MTB H37Rv. GFP fluorescence was measured with Multi-label Plate Reader using the bottom read mode, with excitation at 485 nm and emission at 535 nm. MIC here is defined as the minimum concentration of drug that inhibits more than 90% of bacteria growth reflected by fluorescence value.

Results

Preliminary analysis of the TB proteome permitted mapping TB drug resistance related genes and Single Nucleotide Polymorphisms (SNPs) to their respective proteins and protein residues. The frequency of drug resistance genes coding for disordered and ordered proteins was compared to the general proportion of disordered proteins in the TB proteome, and the frequency of drug resistance SNPs modifying residues in proximity to disordered residues was compared to the general proportion of disordered residues in the TB proteome. These results indicate a close association between TB drug resistance and protein disorder on both the gene level ($p<1.349*10^{-10}$) and the SNP level ($p<5.559*10^{-7}$). As such, a strong relationship is observed between drug resistance and IDPs within TB, indicating that protein disorder and drug resistance are closely linked within *Mycobacterium tuberculosis*. These findings indicate that proteins within TB with known disordered regions and relationship to drug disorder are ideal targets for drug development.

The proteins 2CCA, 2O03, and 2X5L, which are coded by the genes katG, furA, and srmRhomolog respectively, were chosen as targets for drug screening due to the presence of disordered residues affected by drug resistance SNPs within these proteins. An in silico docking process was performed with a comprehensive chemical compound library, which identified several small molecule candidates predicted to bind with these proteins[3]. A visualization of the simulated binding with the top performing compound (CAS 118498-98-9) is shown in FIG. 1. Table 2 shows the list of compounds that were chosen based upon their predicted ability to bind with specific disordered residues on the target TB proteins. NSC260594 and NSC227186 performed at levels comparable of isoniazid and rifampicin (Table 3). It is thought that by affecting the regions which allow such proteins to act as central hubs in biochemical interactions, their function in TB could be inhibited.

Top compounds from the virtual screening process were selected for biological validation on the *Bacillus* Calmette-Guérin (BCG) *Mycobacterium bovis* strain. BCG is an established model for Mtb drug-screening (see, e.g., Ozeki et al. PLoS One 2015 10:e0141658; Altaf et al. Tuberculosis (Edinb.) 2010 90:333-337; and Shawar et al. Antimicrob Agents Chemother 1997 41:570-574; each of which is incorporated by reference herein in its entirety). Several compounds were observed to demonstrate significant inhibitory behavior at concentrations of 128 ug/mL or less, as shown in Table 2. These compounds outperformed both Isoniazid and Rifampin, today's drugs of choice, in drug resistant TB strains, which was confirmed in a validation experiment.

Further investigation was performed on the top-performing compound CAS 118498-98-9 through inhibition testing on six clinical *Mycobacterium tuberculosis* strains, including those which are resistant to both Rifampin and Isoniazid. The MIC of CAS 118498-98-9 is shown in relation to that of Isoniazid and Rifampin in Table 1. While Rifampin and Isoniazid required concentration increases of more than 30-fold to inhibit the drug resistant strains, CAS 118498-98-9 required only a four-fold increase, validating its ability to successfully inhibit drug resistant strains of *Mycobacterium tuberculosis.*

Further investigation was performed on top-performing compounds from the BCG validation experiments through inhibition testing on both drug resistant and susceptible *Mycobacterium tuberculosis* strains, as well as other *Mycobacterium* species closely related to TB. A comparison between performances on Mtb and closely related strains can demonstrate the specificity of the identified compounds towards TB versus other *Mycobacterium*, providing evidence for the specific binding hypothesized between the identified compounds and TB proteins.

The MIC of selected compounds on TB strains can be seen in Table 4 while the MIC of selected compounds on related strains can be seen in Table 5. As can be seen, the selected compounds can inhibit drug resistant TB growth at levels similar to their MIC for drug susceptible TB, which validates the hypothesis that these selected compounds would be effective in MDR/XDR TB treatment. In addition, the MIC of the selected compounds on *Mycobacterium* strains closely related to TB is much higher than their MICs for TB strains. This demonstrates a significant specificity towards TB inhibition in these compounds.

CONCLUSION

This study provided statistical evidence of a strong association between disordered proteins and TB drug resistance. Specifically, the results found that SNPs affecting TB drug resistance have a much higher frequency of occurrence in disordered residues than ordered residues. This finding validates the original hypothesis that IDPs play important roles in the biological functions of *Mycobacterium tuberculosis*, and specifically within processes that result in the evolution of drug resistance. As such, IDPs coded for by genes with known effects on TB drug resistance are likely crucial for the development of TB drug resistance. Therefore, compounds capable of interfering with these protein functions are able to inhibit MDR/XDR-TB growth and be used as new anti-MDR-TB drugs.

The biological validation for our test case of TB was dramatic: newly identified compounds were observed to inhibit TB growth at levels competitive with currently employed drugs.

TABLE 1

Minimum Inhibitory Concentration (MIC) of Rifampin, Isoniazid, and CAS 118498-98-9 on six different TB strains. Hs represents Isoniazid susceptible, Rs represents Rifampin susceptible, Hr represents Isoniazid resistant, and Rr represents rifampin resistant strains.

| | MIC (ng/mL) | | | | | |
|---|---|---|---|---|---|---|
| Compound | $H^sR^s$ 90# | $H^sR^s$ 140# | $H^sR^s$ 74# | $H^rR^r$ 77# | $H^rR^r$ 76# | $H^rR^r$ 80# |
| CAS 118498-98-9 | 6400 | 3200 | 6400 | 3200 | 25600 | 25600 |

TABLE 2

Compounds identified by the drug screening process, their target proteins, and MIC from in vitro validation

| Compound Name | Target Protein | MIC (ug/mL) |
|---|---|---|
| CAS 118498-98-9 | PDB 2X5L | 32 |
| CAS 376374-34-4 | PDB 2X5L, 3PTY | 128 |
| CAS 353779-33-6 | PDB 2CCA, 3PTY | 128 |
| CAS 355816-45-4 | PDB 2X5L, 2CCA | 128 |
| CAS 333759-52-7 | PDB 2X5L, 2CCA, 3PTY, 2003 | >128 |
| CAS 1164528-69-1 | PDB 2003 | >128 |
| CAS 292169-72-3 | PDB 2X5L | >128 |

TABLE 3

Compounds identified by the drug screening process, their target proteins, and Minimum Inhibitory Concentration (MIC) from in vitro validation on Bacillus Calmette-Guérin (BCG)

| Compound Name | MIC (ug/mL) |
|---|---|
| NSC 260594 | 0.078 |
| NSC 227186 | 0.625 |
| NSC 270738 | 5 |

TABLE 3-continued

Compounds identified by the drug screening process, their target proteins, and Minimum Inhibitory Concentration (MIC) from in vitro validation on Bacillus Calmette-Guérin (BCG)

| Compound Name | MIC (ug/mL) |
|---|---|
| NSC 61610 | 40 |
| NSC 37219 | 80 |
| NSC 80731 | 80 |

TABLE 4

Minimum Inhibitory Concentration (MIC) of selected compounds on drug susceptible and drug resistant *Mycobacterium tuberculosis* strains.

| | MIC (ug/mL) | | |
|---|---|---|---|
| | Susceptible | Drug Resistant | |
| Compound | H37Rv | LZ94 | LZ99 |
| NSC 260594 | <0.625 | 0.625 | 1.25 |
| NSC 227186 | <0.625 | 0.625 | 0.625 |

TABLE 5

Minimum Inhibitory Concentration (MIC) of selected compounds on closely related bacteria to tuberculosis

| | MIC (ug/mL) | | | | | |
|---|---|---|---|---|---|---|
| Compound | M. xenopi BZ-23 | M. cheelonae BZ-4 | M. abscessus BZ-24 | M. avium A209 | M. terrae BZ-15 | M. scrofulaceum BZ-20 |
| NSC 260594 | >80 | >80 | >80 | 1.25 | 2.5 | >80 |
| NSC 227186 | 80 | 40 | 40 | 80 | >80 | 80 |

REFERENCES

1 Hsu, W. L. et al. Exploring the binding diversity of intrinsically disordered proteins involved in one-to-many binding. Protein science: a publication of the Protein Society 22, 258-273, doi:10.1002/pro.2207 (2013).
2 Anurag, M. & Dash, D. Unraveling the potential of intrinsically disordered proteins as drug targets: application to *Mycobacterium tuberculosis*. Molecular bioSystems 5, 1752-1757, doi:10.1039/B905518p (2009).
3 Ward, J. J., Sodhi, J. S., McGuffin, L. J., Buxton, B. F. & Jones, D. T. Prediction and functional analysis of native disorder in proteins from the three kingdoms of life. Journal of molecular biology 337, 635-645, doi:10.1016/j.jmb.2004.02.002 (2004).
4 Jones, G., Willett, P., Glen, R. C., Leach, A. R. & Taylor, R. Development and validation of a genetic algorithm for flexible docking. Journal of molecular biology 267, 727-748, doi:10.1006/jmbi.1996.0897 (1997).
5 Disfani, F. M. et al. MoRFpred, a computational tool for sequence-based prediction and characterization of short disorder-to-order transitioning binding regions in proteins. Bioinformatics 28, i75-83, doi:10.1093/bioinformatics/bts209 (2012).
6 Uversky, V. N., Oldfield, C. J. & Dunker, A. K. Intrinsically disordered proteins in human diseases: introducing the D2 concept. Annual review of biophysics 37, 215-246, doi:10.1146/annurev.biophys.37.032807.125924 (2008).
7 Dunker, A. K. & Kriwacki, R. W. The orderly chaos of proteins. Scientific American 304, 68-73 (2011).
8 WHO global tuberculosis control report 2010. Summary. Central European journal of public health 18, 237 (2010).
9 Dalton, T. et al. Prevalence of and risk factors for resistance to second-line drugs in people with multidrug-resistant tuberculosis in eight countries: a prospective cohort study. Lancet 380, 1406-1417, doi:10.1016/50140-6736(12)60734-X (2012).
10 Zhao, Y. et al. National survey of drug-resistant tuberculosis in China. The New England journal of medicine 366, 2161-2170, doi:10.1056/NEJMoa1108789 (2012).
11 Dye, C., Scheele, S., Dolin, P., Pathania, V. & Raviglione, M. C. Consensus statement. Global burden of tuberculosis: estimated incidence, prevalence, and mortality by country. WHO Global Surveillance and Monitoring Project. JAMA: the journal of the American Medical Association 282, 677-686 (1999).
12 Lew, J. M., Kapopoulou, A., Jones, L. M. & Cole, S. T. TubercuList—10 years after. Tuberculosis 91, 1-7, doi:10.1016/j.tube.2010.09.008 (2011).
13 Sandgren, A. et al. Tuberculosis drug resistance mutation database. PLoS medicine 6, e2, doi:10.1371/journal.pmed.1000002 (2009).
14 Dessen, A., Quemard, A., Blanchard, J. S., Jacobs, W. R., Jr. & Sacchettini, J. C. Crystal structure and function of the isoniazid target of *Mycobacterium tuberculosis*. Science 267, 1638-1641 (1995).

Example 2: Targeting Intrinsically Disordered Regions in the *M. Tuberculosis* Proteome to Identify Novel Therapeutic Strategies Against Drug-Resistant TB Multidrug drug-resistant tuberculosis (MDR-TB) evades the two most powerful anti-TB drugs, isoniazid and rifampicin. Just two years ago, the number of reported cases of multidrug-resistant tuberculosis approached half a million worldwide. The World Health Organization estimates that about 9.5 percent of these cases were extensively drug-resistant tuberculosis (XDR-TB), a strain that renders even second-line drugs ineffective.

Described herein are high throughput assays to identify anti-TB compounds against bacille Calmette-Guerin (BCG) and *Mycobacterium tuberculosis* (MTB) clinical isolates. From a library of more than 4,000 small molecules, 3 compounds were selected, including one synthesized compound (referred to as NSC 260594 or Formula XI).

Formula XI is a quinolinium derivative similar in structure to known DNA binding compounds. It shows significant anti-TB activity against susceptible H37Rv strain. (MIC value of Rifampicin=0.1 m/ml) and MIC value was <0.625 μg/ml.) Its activity has been further tested against two MDR-MTB isolates LZ94 and LZ99 with MIC value of Rifampicin increased to 2 μg/ml. These results showed that it would also kill drug-resistant strains with the MIC values 0.625 μg/ml for LZ94 and 1.25 μg/ml for LZ99 (Table 7).

TABLE 7

| Compound | MIC (μg/ml) | | |
| --- | --- | --- | --- |
| | Susceptible | Drug Resistant | |
| | H37Rv | LZ94 | LZ99 |
| NSC 260594 | <0.625 | 0.625 | 1.25 |

Figure 3A:
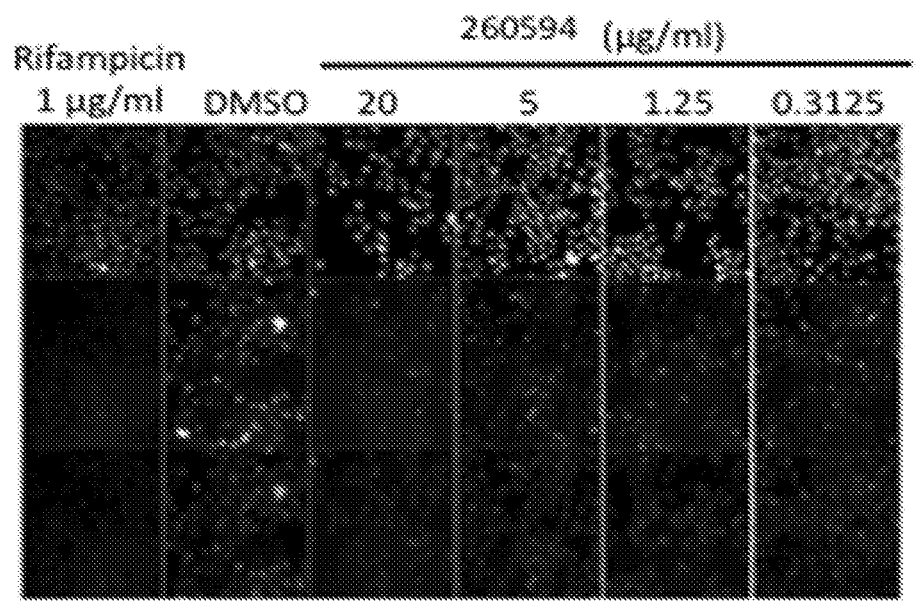
FIGS. 3A-3B depict imaging assay for in vivo anti-infective activity characterization for Formula XI.
Figure 3B:
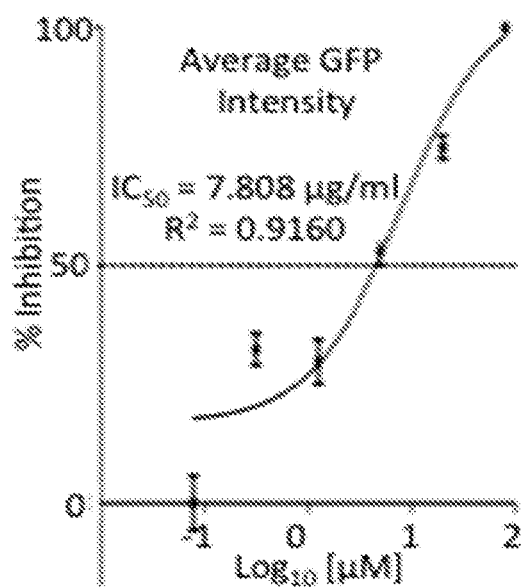

The compound of Formula XI was further characterized due to its significant performance on suppressing growth in THP-1 cells. A microscopy-based assay as developed to permit simultaneous imaging of macrophages and mycobacteria. As shown in FIG. 3A, a high-content imaging assay was carried out to monitor the growth of GFP-expressing BCG in infected THP-1 cells. Compared to spectrophotometer readings, image analysis provides better sensitivity with respect to bacterial growth inhibition, while at the same time establishing the compound's significant macrophage toxicity. The results clearly demonstrate an in vivo anti-infective effect of the molecule in a dose-dependent manner (plotted in FIG. 3B), with an IC50 of 7.8 μg/ml.

MTT assay was performed to test the cytotoxicity of the compound of Formula XI. The compound proved to be less toxic to macrophage cell line THP-1 than Rifampicin (anti-TB drug) in our BCG-macrophage system (Table 8).

TABLE 8

| Drugs | IC50(μg/ml) |
| --- | --- |
| Compound 1 = Formula XI = NSC 260594 | 7.5 |
| Rifampicin | 1.0 |

Figure 4:
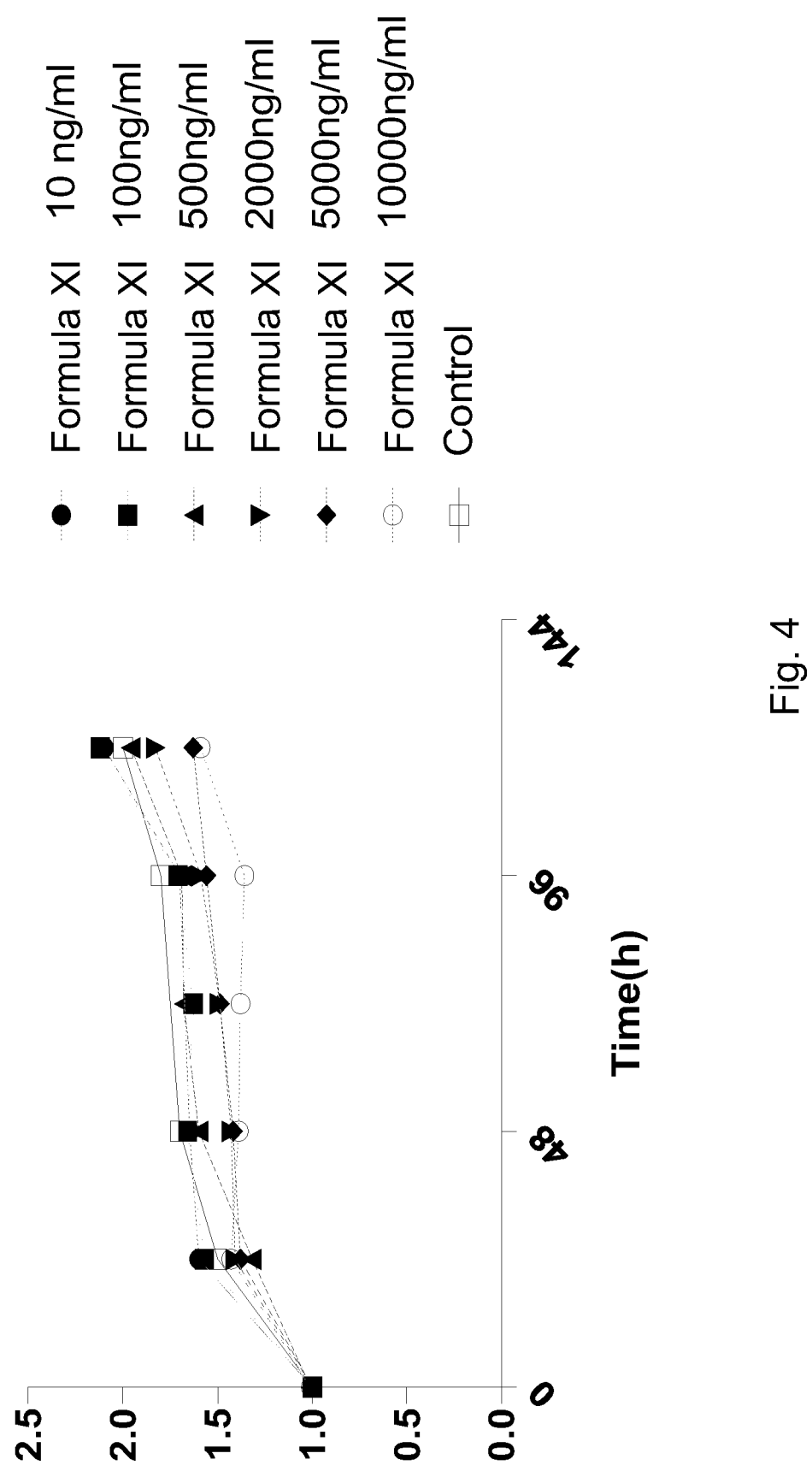
FIG. 4 depicts a graph demonstrating that the compound of Formula XI exhibited time and concentration-dependent activity intracellularly.

The assay system described herein was optimized based on published assays measuring the pharmacodynamic response of intracellular BCG within macrophages to Rifampicin, the result agreed with reference reported. The compound of Formula XI exhibited time- and concentration-dependent anti-TB activity intracellularly against BCG (FIG. 4).

Figure 5:
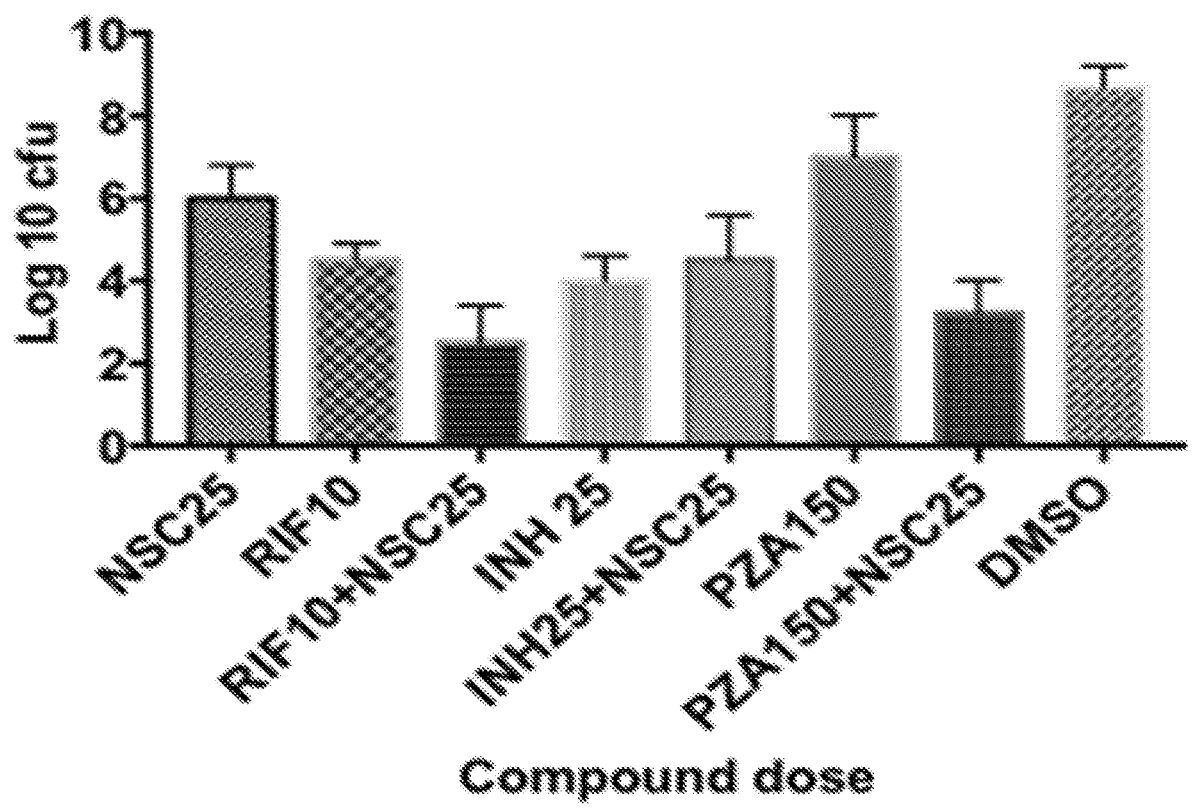
FIG. 5 depicts a graph of colony forming units in BCG when treated with NSC 260594 (25 μg/ml) combined with clinical drugs. RIF 10: Rifampicin (10 μg/ml), PZA150: Pyrazinamide (150 μg/ml), INH 25: Isoniazid (25 μg/ml)
Figure 6:
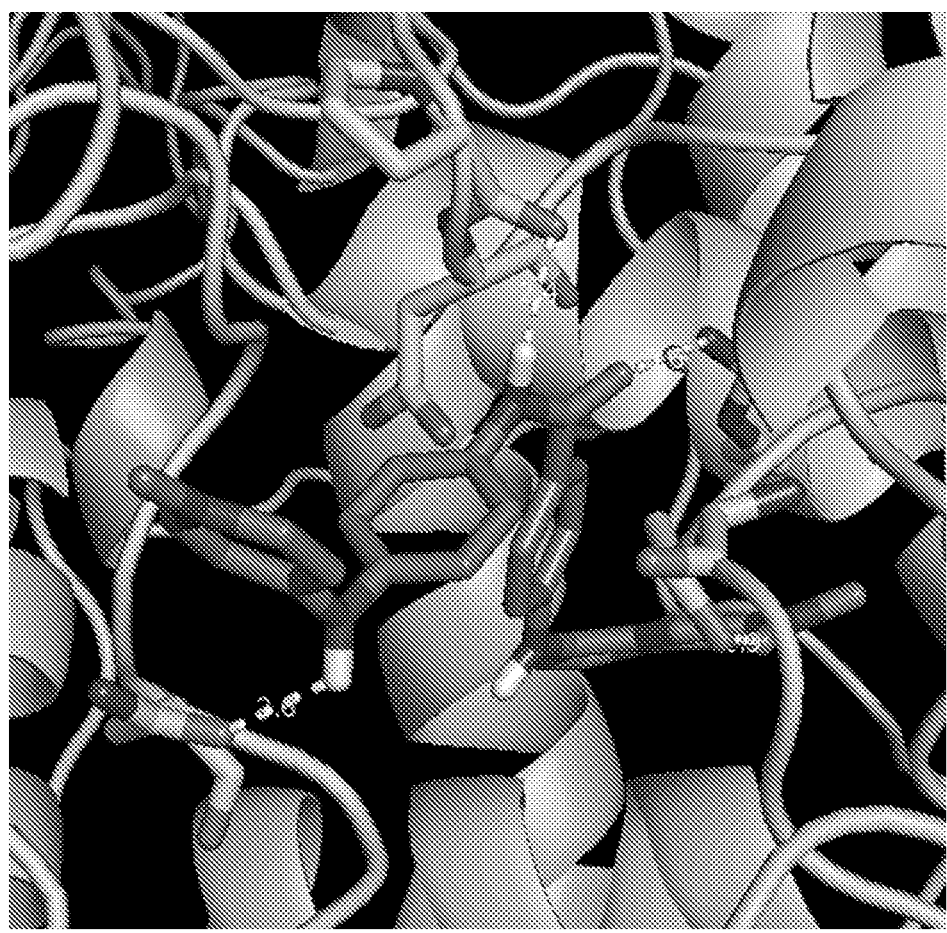
FIG. 6 depicts a binding simulation of compound with KatG S315T mutation

The compound's in vivo effectiveness in combination with current first and second line anti-tuberculosis drugs and synergism was demonstrated (FIG. 5). CFU decreased when the compound of Formula XI (NSC 260594) was mixed with other drugs, indicating a synergistic effect as NSC 260594 and the other drug targets are different. NSC 260594 can overcome INH resistance by covering both potential binding sites in KatG S315T (FIG. 6).

What is claimed is:
1. A method of treating tuberculosis in a subject, the method comprising administering to the subject a composition comprising at least one compound selected from the group consisting of:

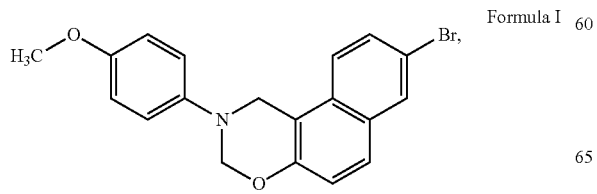

Formula I

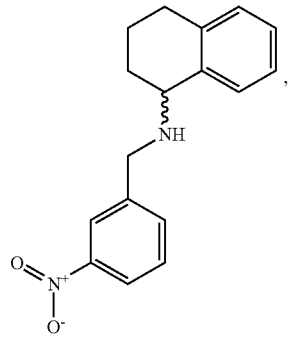

Formula II

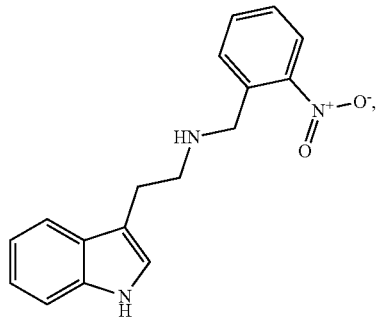

Formula III

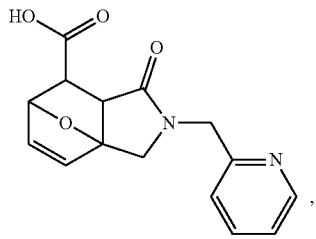

Formula IV

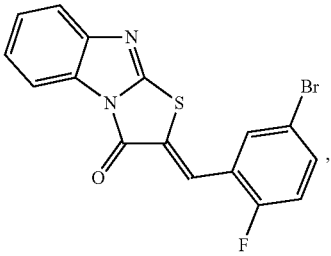

Formula V

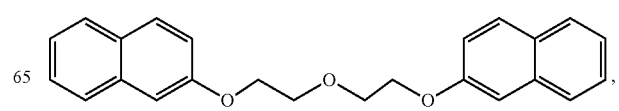

Formula VI

Formula VII

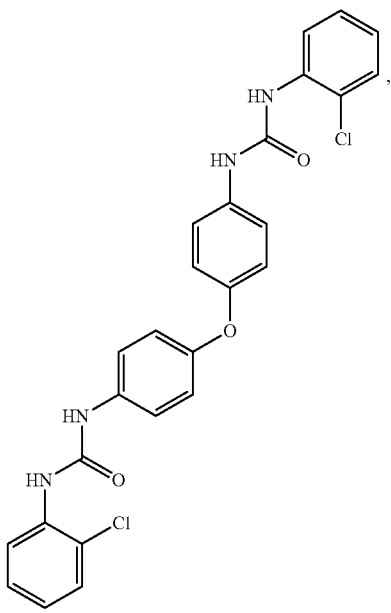

Formula VIII

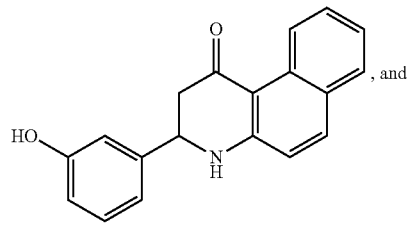, and

Formula IX

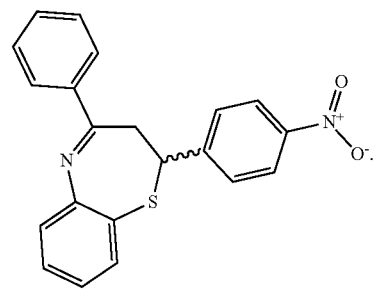

2. The method of claim 1, wherein the subject is further administered, or the composition further comprises a compound selected from the group consisting of:

Formula X

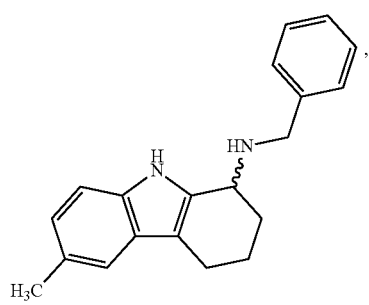,

Formula XI

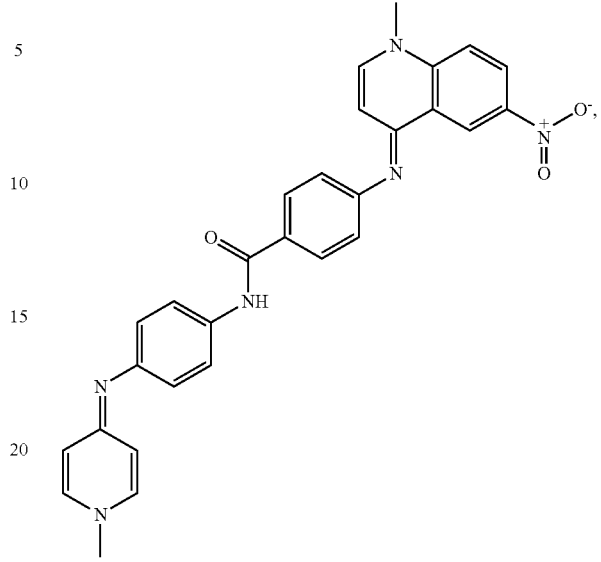

Formula XII

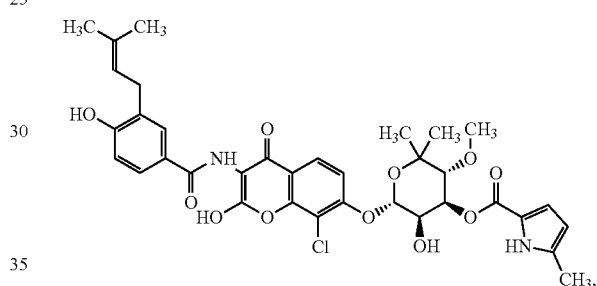

and

Formula XIII

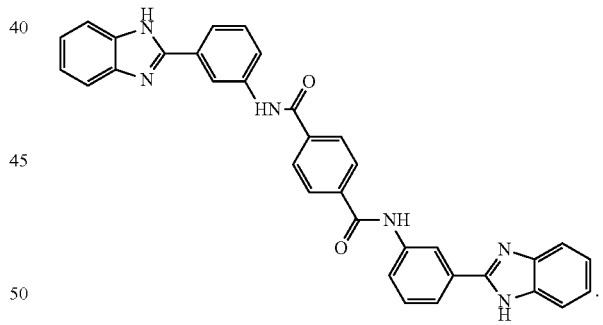

3. The method of claim 1, wherein the tuberculosis is drug-resistant tuberculosis.
4. The method of claim 3, wherein the tuberculosis is multiple drug-resistant tuberculosis.
5. The method of claim 3, wherein the tuberculosis is extensively drug-resistant tuberculosis.
6. A composition comprising at least two compounds selected from the group consisting of Formulas I-IX.
7. The composition of claim 6, further comprising at least one compound selected from the group consisting of Formulas X-XIII.
8. A method of treating tuberculosis in a subject, the method comprising administering to the subject
   a) at least one compound selected from the group consisting of:

Formula I
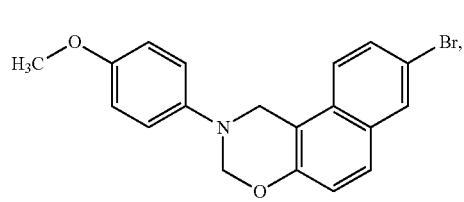
Formula II
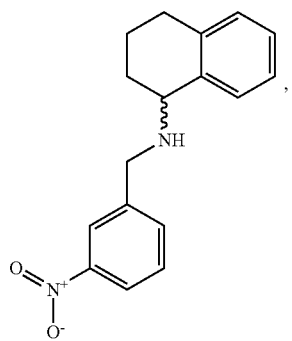
Formula III
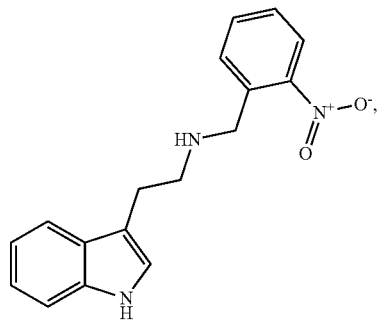
Formula IV
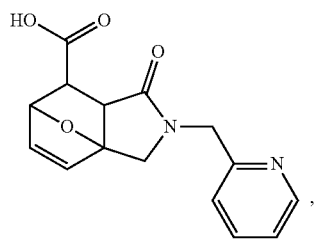
Formula V
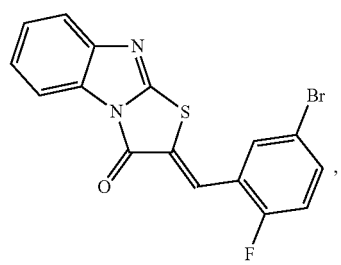
Formula VI
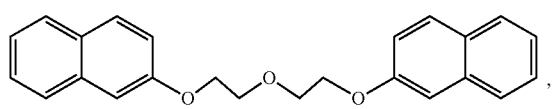
-continued
Formula VII
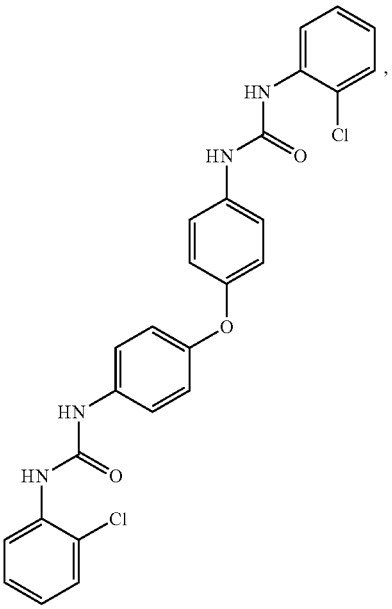
Formula VIII
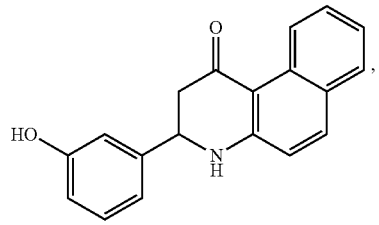
Formula IX
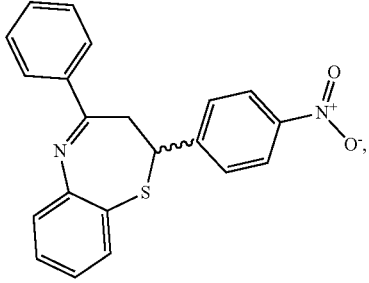
Formula X
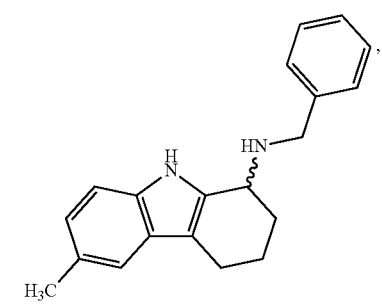

Formula XI

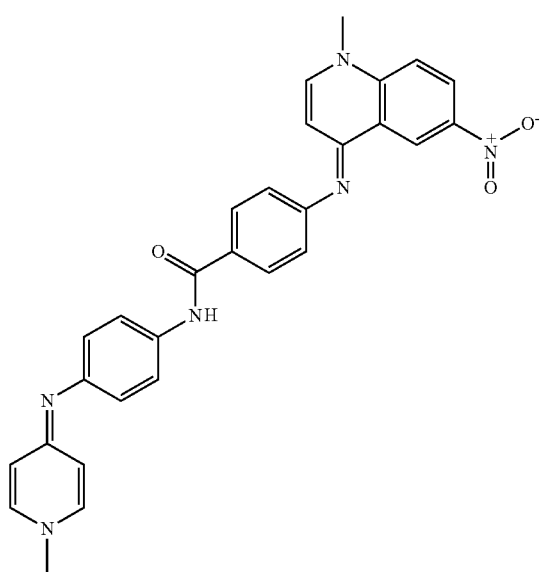

Formula XII

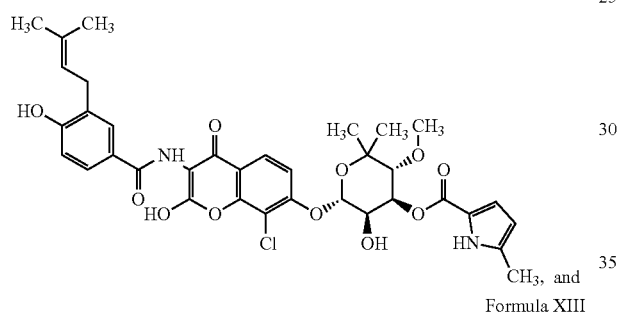

Formula XIII

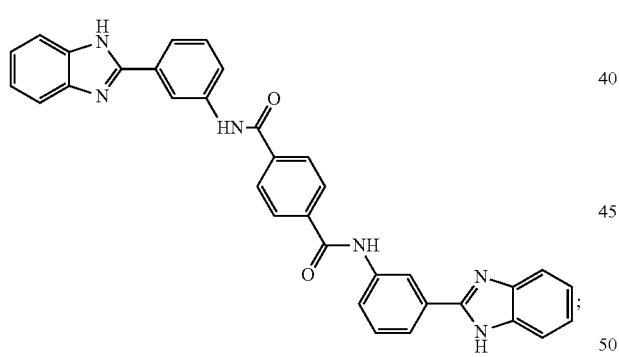

and
b) at least one compound selected from the group consisting of rifampicin or pyrazinamide.

9. The method of claim 8, wherein the tuberculosis is drug-resistant tuberculosis.

10. The method of claim 9, wherein the tuberculosis is multiple drug-resistant tuberculosis.

11. The method of claim 9, wherein the tuberculosis is extensively drug-resistant tuberculosis.

12. The method of claim 8, wherein the compounds of a) and b) are administered separately.

13. The method of claim 8, wherein the compounds of a) and b) are administered concurrently.

14. A method comprising administering to a subject with tuberculosis a composition comprising at least one compound selected from the group consisting of:

Formula I

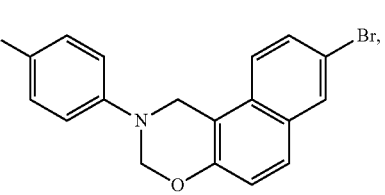

Formula II

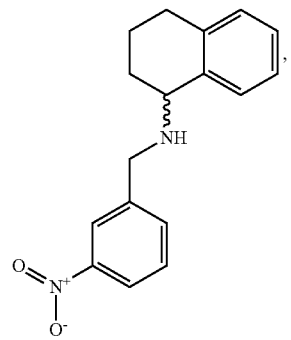

Formula III

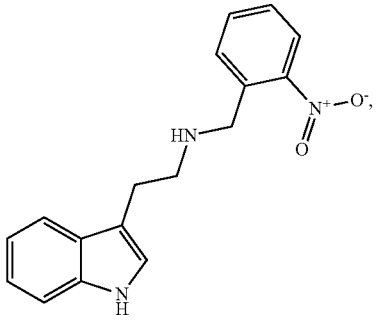

Formula IV

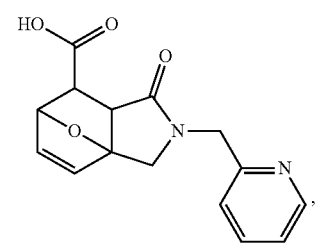

Formula V

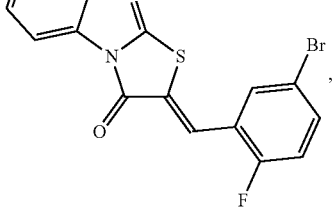

Formula VI

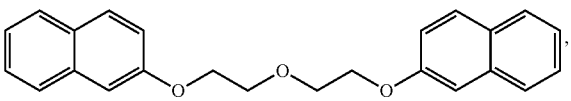

Formula VII

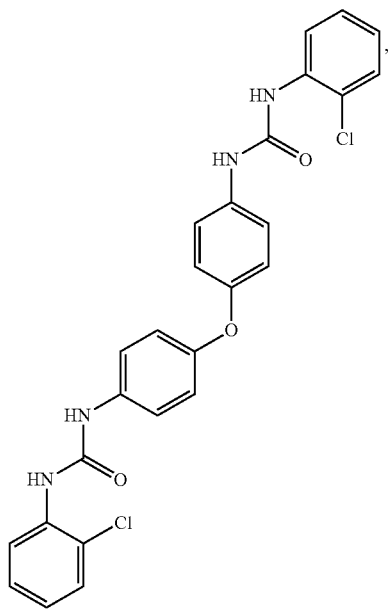

Formula VIII

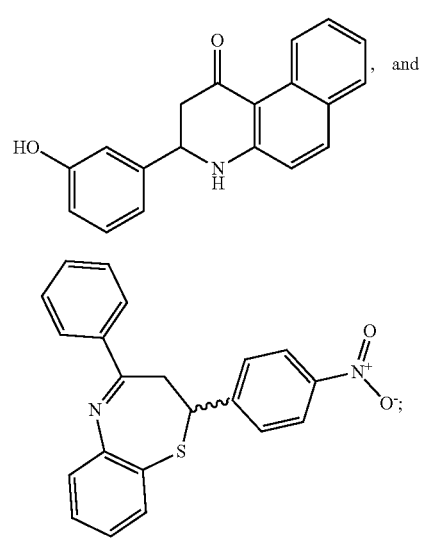
, and

Formula IX whereby the growth of a *Mycobacterium tuberculosis* in the subject is inhibited.

15. The method of claim 14, wherein the subject is further administered, or the composition further comprises a compound selected from the group consisting of:

Formula X

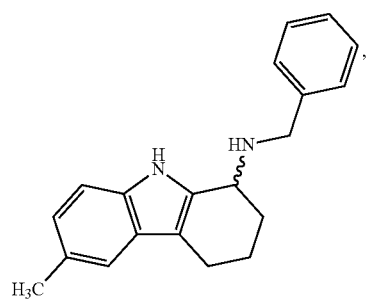
,

Formula XI

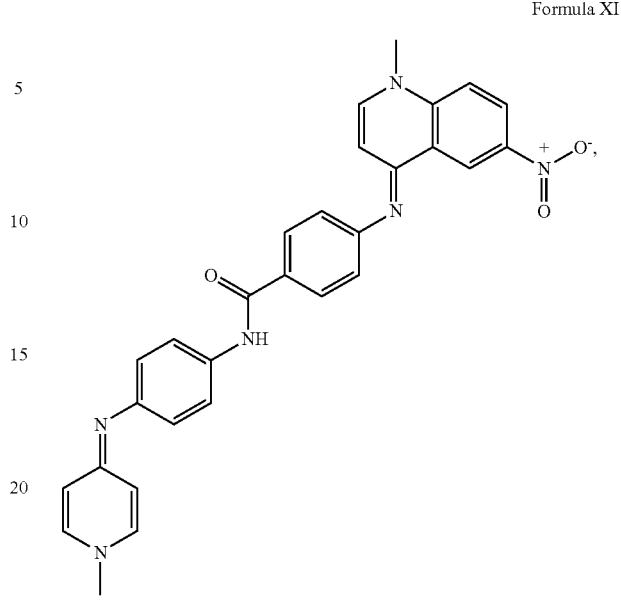

Formula XII

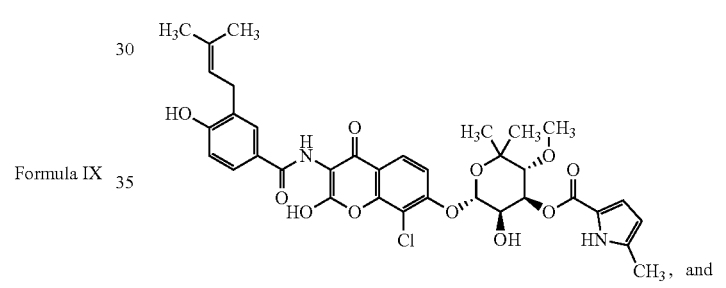
, and

Formula XIII

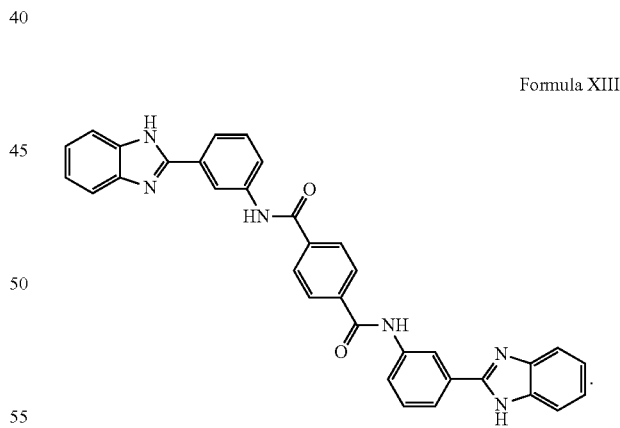
.

16. The method of claim 14, wherein the tuberculosis is drug-resistant tuberculosis.
17. The method of claim 16, wherein the tuberculosis is multiple drug-resistant tuberculosis.
18. The method of claim 16, wherein the tuberculosis is extensively drug-resistant tuberculosis.
19. A method comprising administering to a subject with tuberculosis:
   a) at least one compound selected from the group consisting of:

Formula I
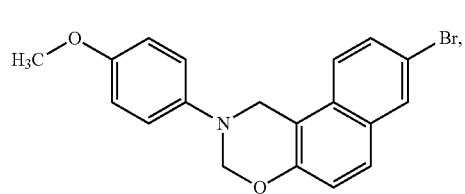
Formula II
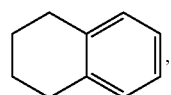
Formula III
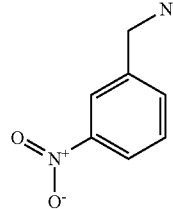
Formula IV
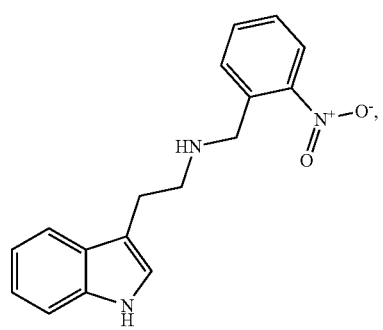
Formula V
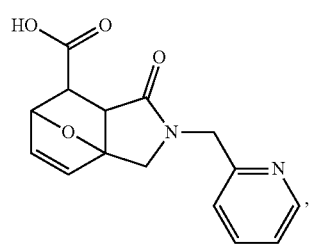
Formula VI
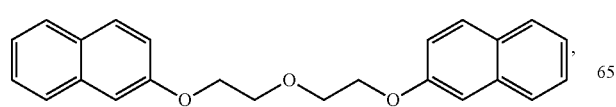
Formula VII
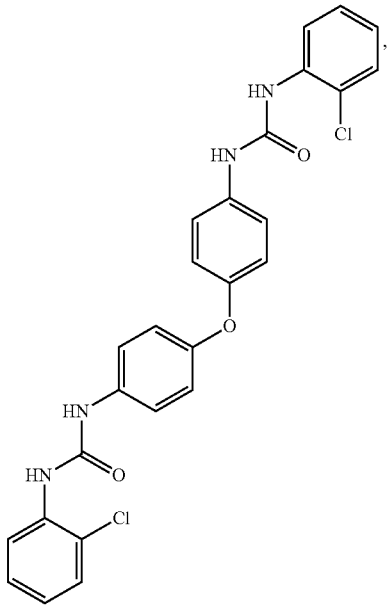
Formula VIII
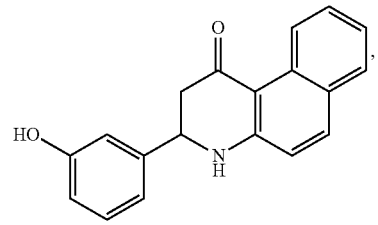
Formula IX
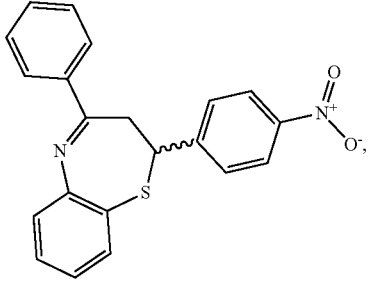
Formula X
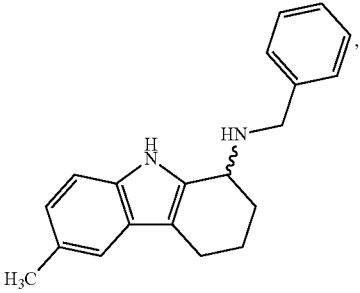

Formula XI

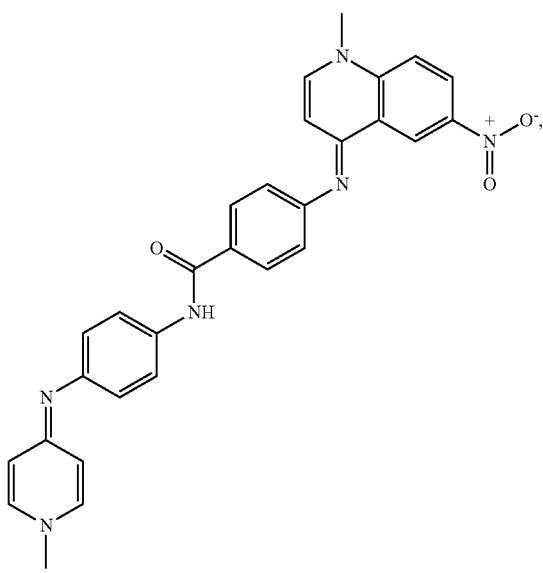

Formula XII

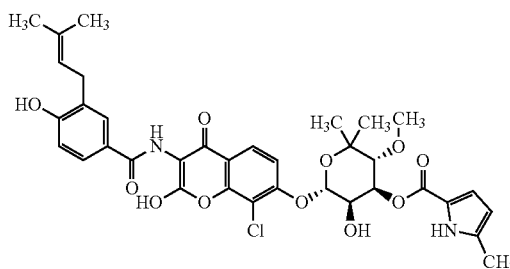

Formula XIII

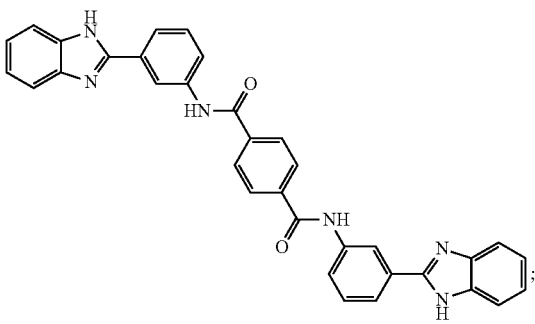

b) at least one compound selected from the group consisting of rifampicin or pyrazinamide; whereby the growth of a *Mycobacterium tuberculosis* in the subject is inhibited.

20. The method of claim 19, wherein the tuberculosis is drug-resistant tuberculosis.

21. The method of claim 20, wherein the tuberculosis is multiple drug-resistant tuberculosis.

22. The method of claim 20, wherein the tuberculosis is extensively drug-resistant tuberculosis.

23. The method of claim 19, wherein the compounds of a) and b) are administered separately.

24. The method of claim 19, wherein the compounds of a) and b) are administered concurrently.

25. The method of claim 1, wherein the administration is oral, by inhalation, intravenous, or intramuscular.

26. The method of claim 14, wherein the administration is oral, by inhalation, intranasal, intravenous, or intramuscular.

27. The method of claim 19, wherein the administration is oral, by inhalation, intranasal, intravenous, or intramuscular.

* * * * *